(12) United States Patent
Subramanian et al.

(10) Patent No.: US 12,094,615 B2
(45) Date of Patent: Sep. 17, 2024

(54) DYNAMIC RISK ASSESSMENT

(71) Applicant: ACCENTURE GLOBAL SOLUTIONS LIMITED, Dublin (IE)

(72) Inventors: Venkatesh Subramanian, Bangalore (IN); Nataraj Kuntagod, Bangalore (IN); Satya Sai Srinivas, Bangalore (IN)

(73) Assignee: ACCENTURE GLOBAL SOLUTIONS LIMITED, Dublin (IE)

( * ) Notice: Subject to any disclaimer, the term of this patent is extended or adjusted under 35 U.S.C. 154(b) by 539 days.

(21) Appl. No.: 17/383,944

(22) Filed: Jul. 23, 2021

(65) Prior Publication Data

US 2022/0051807 A1 Feb. 17, 2022

(30) Foreign Application Priority Data

Jul. 29, 2020 (IN) .............................. 202011032516

(51) Int. Cl.
*G06F 7/02* (2006.01)
*G06F 16/00* (2019.01)
*G06F 16/28* (2019.01)
*G06N 20/00* (2019.01)
*G06V 20/10* (2022.01)
*G06V 40/20* (2022.01)
*G16H 50/80* (2018.01)

(52) U.S. Cl.
CPC ........... *G16H 50/80* (2018.01); *G06F 16/283* (2019.01); *G06N 20/00* (2019.01); *G06V 20/10* (2022.01); *G06V 40/20* (2022.01)

(58) Field of Classification Search
CPC ...... G16H 50/80; G06N 20/00; G06F 16/283; G06V 20/10; G06V 40/20
See application file for complete search history.

(56) References Cited

U.S. PATENT DOCUMENTS

| 10,706,970 | B1 | 7/2020 | Florissi et al. |
| 2013/0318027 | A1 | 11/2013 | Almogy et al. |
| 2017/0024531 | A1 | 1/2017 | Malaviya |
| 2019/0252078 | A1 | 8/2019 | Schubert et al. |
| 2021/0050113 | A1* | 2/2021 | Harle ..................... G16H 50/20 |
| 2022/0027565 | A1* | 1/2022 | Klasson ................. G16H 50/80 |

FOREIGN PATENT DOCUMENTS

| WO | 2017/216056 | 12/2017 |
| WO | 2020/046398 | 3/2020 |

* cited by examiner

*Primary Examiner* — Bruce M Moser
(74) *Attorney, Agent, or Firm* — Mannava & Kang, P.C.

(57) ABSTRACT

A system and method for dynamic risk assessment is disclosed. The system may include a data warehouse, an output device and a processor including a data capturer, a process engine and a rules engine. The data capturer may capture information pertaining to a plurality of risk factors associated with an infection risk corresponding to a plurality of data elements in an environment. The plurality of data elements may pertain to at least one of a space and a person in the space. The process engine may include at least one of a space risk profiler and a person risk profiler. The process engine may determine a risk score and a risk profile associated with the person and the space. Based on the risk profile, the processor may perform at least one of an automatic identification of a mitigation to reduce the infection risk and an automated generation of an alert.

18 Claims, 11 Drawing Sheets

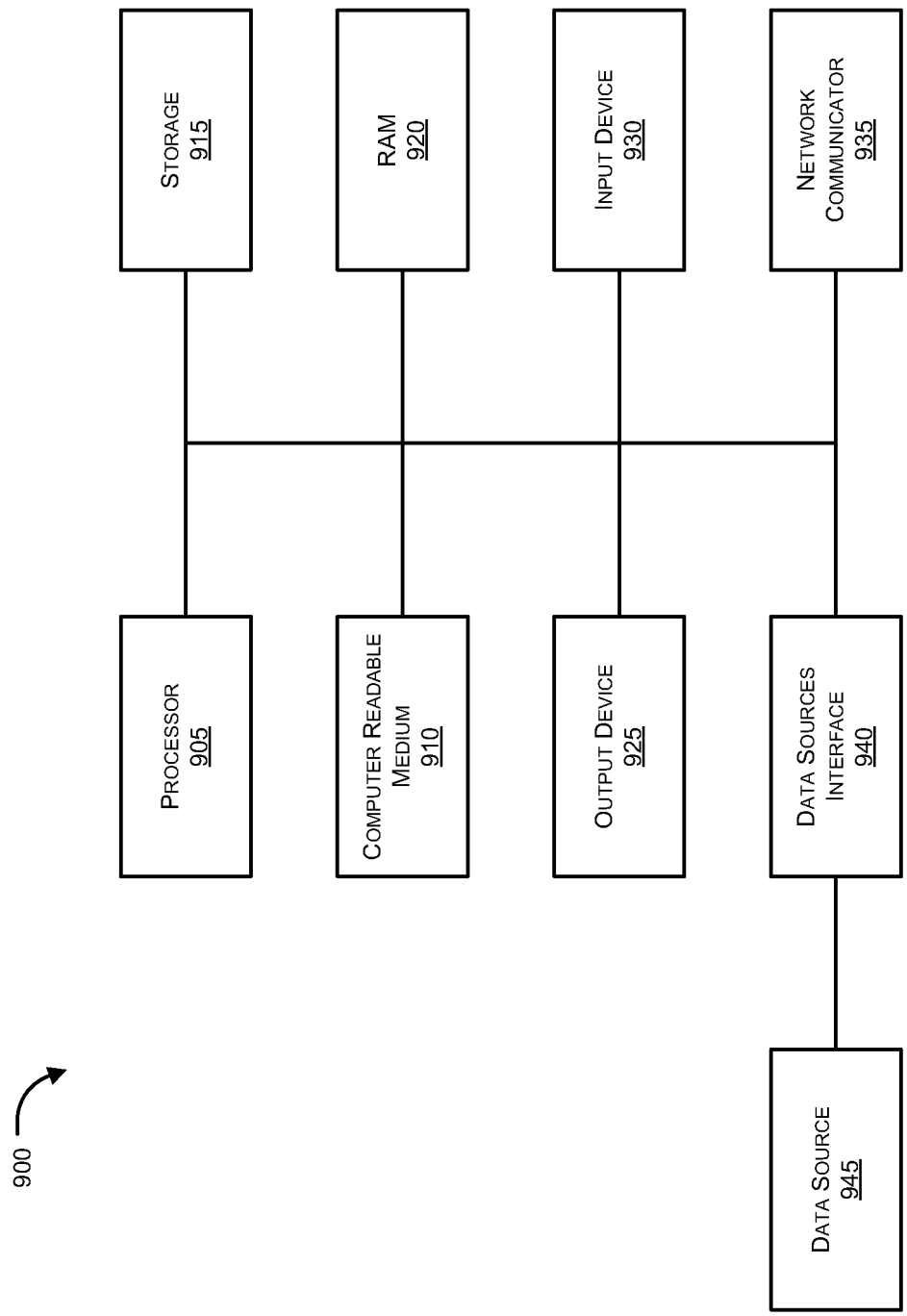

DYNAMIC RISK ASSESSMENT

PRIORITY CLAIM

The present application claims priority to Indian Patent Application Number 202011032516 filed on Jul. 29, 2020, the disclosure of which is incorporated by reference in its entirety.

BACKGROUND

Mankind has been struggling with epidemics and infectious diseases since pre-historic times. The infectious diseases caused by various microscopic organisms such as, for example, a virus, a bacteria, a protozoa, and the like have been consistently giving rise to pandemics. Examples of viruses that may cause such diseases include various types of respiratory viruses. These viruses are known to cause cold or other respiratory illnesses in humans. Some viruses can cause serious diseases like severe acute respiratory syndrome (SARS) and Middle East Respiratory Syndrome (MERS). One of the latest examples is the recent outbreak is severe acute respiratory syndrome coronavirus 2 (referred to as "Covid-19" hereinafter), which can cause symptoms, ranging from mild illness like fever, cough, sore throat and headache, to potentially serious ones, such as pneumonia. In severe cases, COVID-19 can cause breathing difficulties and death.

Disease causing agents, i.e., pathogens, may be primarily transmitted through respiratory droplets, by direct contact with infected persons, or by contact with contaminated objects and surfaces. Therefore, strategies to mitigate risk of transmission of such pathogens include limiting close contacts between people and use of barrier precautions against exposure to droplets. However, as incubation period of pathogens may range from days to weeks, the risk of spreading the pathogen by undetected or asymptomatic cases may be high. For example, for certain viruses the incubation period may be from 1-14 days with median estimates of 5-6 days between infection and the onset of clinical symptoms of a disease. In addition, risk of transmission of pathogens and infection may be higher in enclosed spaces, such as work places, as an asymptomatic carrier or an infected person may expose himself to other people thereby creating a high risk environment.

In such scenarios, risk identification, mitigation, and comprehensive alerting is extremely critical to limit the spread of the infectious diseases. In order to assess and mitigate the risks, available systems may provide contact tracing. In such systems, users are notified based on pre-set criteria, for example, if they were within two meters of an infected person and if that contact took place over an extended period of time. However, most of these systems are suitable for outdoor use and require GPS data to operate. Moreover, these systems merely carry out contact tracing to alert users if they are in proximity of an infected person. In addition, these systems generally operate at a coarse level of granularity and do not provide any strategy that can work at a fine level of granularity, for work places like offices and factories. For example, available systems may recommend shutting down an entire factory or workspace, if an infected person is identified, instead of precisely locating an infected area(s) and sanitizing the area(s). This may lead to unnecessary wastage of time and loss of capital.

SUMMARY

An embodiment of present disclosure includes a system including a processor. The processor may include a data capturer, a process engine and a rules engine. The system may also include a data warehouse and an output device. The data capturer may capture information pertaining to a plurality of risk factors associated with an infection risk. The infection risk may correspond to a plurality of data elements in an environment. The plurality of data elements may pertain to at least one of a space and a person in the space. The data warehouse may be coupled to the processor and may store the captured information. The process engine may include at least one of a space risk profiler and a person risk profiler. The process engine may determine a risk score associated with the infection risk corresponding to the plurality of data elements. The risk score may include a space risk score corresponding to the space and a person risk score associated with the person. The risk score may be a weighted function of the corresponding risk factors. Using the space risk profiler, the process engine may determine, based on the space risk score, a space risk profile associated with the space. Using the person risk profiler, the process engine may determine, based on the person risk score, a person risk profile associated with the person. The process engine may be coupled to the data warehouse to automatically update the space risk profile and the person risk profile. Based on the risk profile, the processor performs at least one of an automatic identification of a mitigation to reduce the infection risk and an automated generation of an alert.

Another embodiment of the present disclosure may include a method for facilitating a dynamic risk assessment. The method may include a step of capturing, by a processor, information pertaining to a plurality of risk factors associated with an infection risk. The infection risk may correspond to a plurality of data elements in an environment. The plurality of data elements may pertain to at least one of a space and a person in the space. The method may include a step of determining, by the processor, a risk score associated with the infection risk corresponding to the plurality of data elements. The risk score may include a space risk score corresponding to the space and a person risk score associated with the person. The risk score may be a weighted function of the corresponding risk factors. The method may include a step of determining, by the processor, based on the space risk score, a space risk profile associated with the space. The method may include a step of determining, by the processor, based on the person risk score, a person risk profile associated with the person. The method may include a step of performing, by the processor, based on the risk profile, at least one of an automatic identification of a mitigation to reduce the infection risk and an automated generation of an alert.

Yet another embodiment of the present disclosure may include a non-transitory computer readable medium comprising machine executable instructions that may be executable by a processor to receive an input data corresponding to a programming language. The processor may capture information pertaining to a plurality of risk factors associated with an infection risk corresponding to a plurality of data elements in an environment. The plurality of data elements may pertain to at least one of a space and a person in the space. The processor may determine a risk score associated with the infection risk corresponding to the plurality of data elements. The risk score may include a space risk score corresponding to the space and a person risk score associated with the person. The risk score may be a weighted function of the corresponding risk factors. The processor may determine, based on the space risk score, a space risk profile associated with the space. The processor may determine, based on the person risk score, a person risk profile associated with the person. The processor may perform, based on the risk profile, at least one of an automatic identification of a mitigation to reduce the infection risk and an automated generation of an alert.

BRIEF DESCRIPTION OF DRAWINGS

Features of the present disclosure are illustrated by way of examples shown in the following figures. In the following figures, like numerals indicate like elements, in which:

FIG. 9 illustrates a hardware platform for the implementation of the dynamic risk assessment system, according to an example embodiment of the present disclosure.

DETAILED DESCRIPTION

Figure 1:
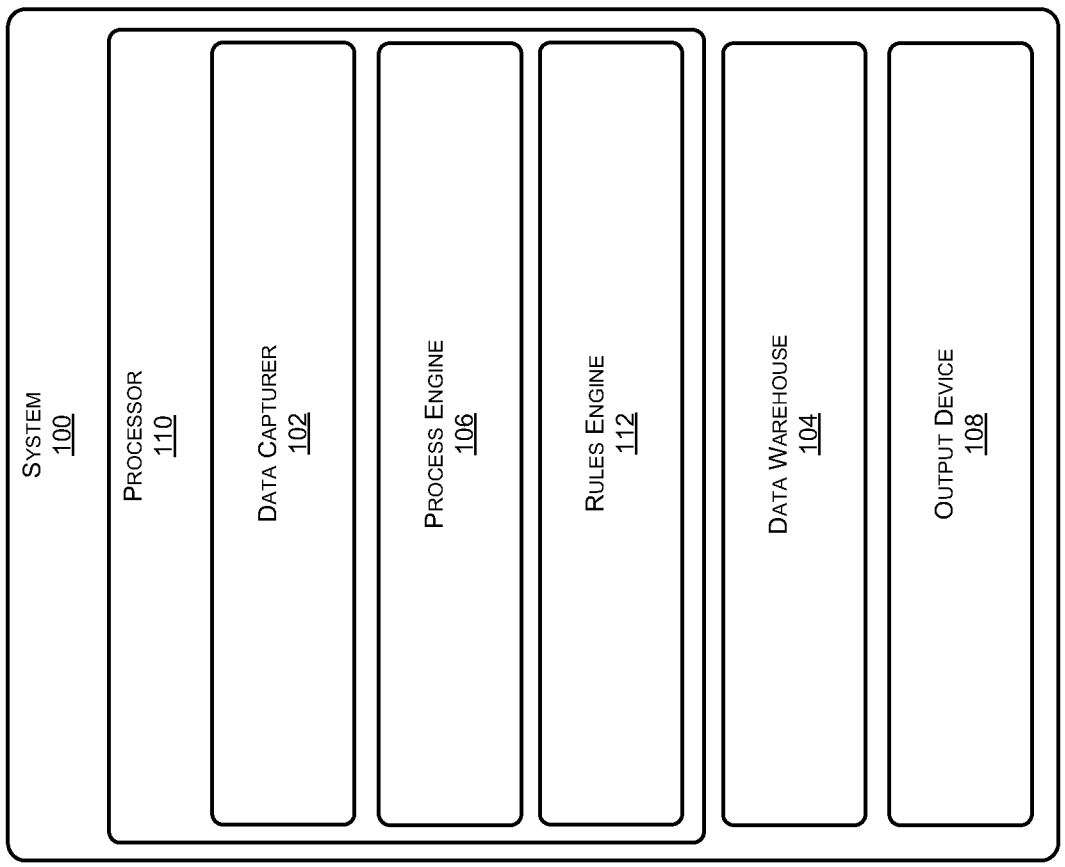
FIG. 1 illustrates a block diagram of a dynamic risk assessment system, according to an example embodiment of the present disclosure.

For simplicity and illustrative purposes, the present disclosure is described by referring mainly to examples thereof. The examples of the present disclosure described herein may be used together in different combinations. In the following description, details are set forth in order to provide an understanding of the present disclosure. It will be readily apparent, however, that the present disclosure may be practiced without limitation to all these details. Also, throughout the present disclosure, the terms "a" and "an" are intended to denote at least one of a particular element. The terms "a" and "a" may also denote more than one of a particular element. As used herein, the term "includes" means includes but not limited to, the term "including" means including but not limited to. The term "based on" means based at least in part on, the term "based upon" means based at least in part upon, and the term "such as" means such as but not limited to. The term "relevant" means closely connected or appropriate to what is being performed or considered.

Various embodiments describe providing a solution in the form of a system and a method for dynamic risk assessment. Exemplary embodiments of the present disclosure have been described in the framework of facilitating a dynamic risk assessment to identify a risk. The risk may be associated with an infection risk due to data elements such as, for example, a space, a person and other such elements. The system and method of the present disclosure facilitate assignment of a risk score and risk profile for the data elements. This may be done to indicate, in real-time, the extent of risk associated with the data elements based on several factors. Based on the generated risk profile, the system and the method can automatically identify a mitigation to reduce the infection risk. The system and the method can also generate an alert to avoid interactions that increase the chances of infection risk. In an example embodiment, the infection risk may be associated with a possibility of infection or an infectious disease and/or spreading of the infection. For example, the infection may be caused by a virus, a bacteria, a protozoa, and the like, especially the risk related to pandemic. Examples of viruses that may cause such diseases include various types of respiratory viruses that are known to cause cold or other respiratory illnesses in humans. Other example may include viruses that can cause serious diseases like severe acute respiratory syndrome (SARS), Middle East Respiratory Syndrome (MERS), severe acute respiratory syndrome coronavirus 2 (referred to as "Covid-19"). In an example embodiment, the system and the method may be implemented within an environment that may be closed or confined. For example, the environment may pertain to space within a home, an office, a workplace, a factory, a research center, a manufacturing unit, an organization, a school, a college and other such places that involves interaction between multiple persons. However, one of ordinary skill in the art will appreciate that the present disclosure may not be limited to such environment or scenarios. The system and the method can also be used for lowering risk in open or semi-open environment and/or situations related to unsafe actions/risks.

The system and method of the present disclosure may determine the extent of risk associated with the data elements based on the risk factors. The risk factors in an environment may be evaluated by considering several aspects. These aspects may be, for example, person-person interactions, person-space interactions and other interactions, person baseline health factors, behavioral factors, and a network-centrality of these factors. For example, the system may analyze multiple person-environment attributes, such as ventilation in the environment being analyzed, a size of the room, a social behavior of a person, such as safe versus unsafe behavior, social behavior of the person inside the environment, attire worn, remedial actions taken, decay of risks, and other such aspects, at various snapshots in time to arrive at a dynamic assessment of the risks. This enables the system of the present disclosure to provide temporal risk scoring of people-people, and people-space interactions using fine granular data. Because various attributes related to not only the environment but the people forming a part of the environment are assessed, the risk assessment performed by the system may be considered as accurate risk assessment.

The system and method of the present disclosure facilitate to mitigate or overcome limitations of the current systems that mainly operate at a coarse level of granularity. For example, an entire section of a factory may be marked unsafe based on just poor hygiene behavior of one person. This can result in red alerts in the entire factory and can eventually lead to closure of factory, which may not be economically feasible. In contrast, the system of the present disclosure is fine grained and can compute risk scores considering very levels of granularity. For example, the system may consider interactions of persons, transit sections of the environment, transit times, and various types of social interactions at multiple snapshots in time as well as risk decays. Such an analysis may result is accurate risk assessment with lower false positives.

FIG. 1A illustrates a system 100 for facilitating a dynamic risk assessment, according to an example embodiment of the present disclosure. In an example embodiment, the dynamic risk assessment system 100 (hereinafter referred to as system 100) amongst other components, includes a processor 110, a data warehouse 104 and an output device 108. The processor 110 incudes a data capturer 102 and a process engine 106 (hereinafter also interchangeably referred to as a "risk assessor"). The processor 110 can also include a rules engine 112. Although, the data warehouse 104 has been illustrated to be internal to the system 100, in other examples, the data warehouse 104 may be external as well. The data capturer 102 may capture information pertaining to a plurality of risk factors associated with an infection risk. In an example embodiment, the data capturer 102 may include at least one of a sensor and a tracking device. The data capturer may be at least one of a Radio-frequency identification (RFID) sensor, Bluetooth™ Low Energy (BLE) sensor, machine learning (ML) based computer vision sensor, a visual sensor, a camera, and a closed-circuit television (CCTV). The present disclosure may not be limited to the mentioned sensors and various other sensors may be used. The infection risk may correspond to a plurality of data elements in an environment. The plurality of data elements may pertain to at least one of a space and a person (also hereinafter interchangeably referred to as "persons" or "people") in the space. The plurality of data elements associated with the space may include at least one of a space transit time data and a building plan data. In an example embodiment, the space transit time data may pertain to a logged time duration spent by the person in the space. The space transit time data may facilitate to evaluate the infection risk in scenarios such as, for example, if an infected person spends a certain time duration in a particular space of the environment. The infected person may refer to an individual who may have contracted the infection already. The space transit time data may also include data related to sanitization of the space and/or prevention of healthy or non-infected persons from entering the space. The building plan data may pertain to at least one of a constructional layout of the space and a list of amenities available in the space. The building plan data may consider the presence of one or more aspects including at least one of an area of the space or ventilation of the space. The list of amenities may relate to checking presence of devices/tools that may limit ventilation, such as, for example, air-conditioning (AC) or devices/tools that may cause improvement in ventilation.

The plurality of data elements associated with the person may include at least one of an attire data, an indoor movement data, an interaction data, hygiene and behavior data, and a network centrality data indicating an extent of social interactions of the at least one person. The attire data may pertain to verification of a recommended attire for the person. For example, it may pertain to a dress code such as wearing masks, personal protective equipment (PPE) and other protective attire to reduce the infection risk. The indoor movement data may pertain to tracked information associated with a path trajectory taken by the person within the space. The interaction data may pertain to a record of an interaction between two or more persons. The hygiene and behavior data may pertain to a behavioral aspect related to maintenance of hygiene by the person (such as, for example, environmental hygiene or personal hygiene/behavior). The network centrality data may pertain to assessment of a social interactive ability of the person. The network centrality data may indicate how central a person may be in a group. For example, in a work place, a team manager may need to interact with a greater number of persons in team in comparison to other team members. Hence, in this example, the team manager may be considered to be more central than the other team members.

The data capturer 102 may capture the information related to the plurality of data elements as mentioned hereinabove. For example, the data capturer 102 may determine the space transit time with the help of the BLE sensor and the RFID sensor. This may be performed by computing an amount of time the person spends or interacts in a particular space. In an example embodiment, the data capturer 102 may capture the attire data by verifying the presence or absence of particular attire of the person with the help of CCTV and computer vision ML sensor. This can be useful in places where standard operating procedures (SOP) require use of the attire including some accessory like face masks, boots, head cap, PPE and the like. The data capturer 102 can capture the presence of the attire or such accessories, which can then be useful in identifying whether the accessories have been used correctly as per operating procedures. Table 1 provides further examples of the information about the data elements, as captured by the data capturer and the manner in which the information is captured. It may be appreciated that the present disclosure may not be limited by the mentioned examples, and several other embodiments/examples are possible.

TABLE 1

Information captured by the data capturer

| Data Element | What is captured | How is it captured |
| --- | --- | --- |
| Space Transit Time | For each person Interacting with a space, the amount of time he/she spends in that space is logged. | Indoor tracking using BLE sensor, RFID sensor is used to capture this time. |
| Person attires | The SOP of the place that may require face masks, boots, head cap, PPE, and the like. Our solution captures the presence and right operating use of these. | CCTV sensor and computer vision ML sensor is used to detect the attires - presence or absence. |
| Building plan | The layout of the workplace, size of rooms/spaces, ventilation, ACs. | This can be a digital building plan fed into system. |

TABLE 1-continued

Information captured by the data capturer

| Data Element | What is captured | How is it captured |
| --- | --- | --- |
| Indoor movement Tracking | The trajectory of paths taken by a user at various points in time | BLE sensor, RFID sensor used to capture the people movements. |
| Interaction data | Who is interacting with whom & where? | BLE sensor, RFID sensor, CCTV sensor |
| Hygiene and Behavior | Hand washing times, space cleaning activity | CCTV sensor, computer vision sensor |
| Network-centrality | How central is a person in the group? More social interactions means more central | Derived from interaction data and social network analysis of people interactions. |

The data warehouse 104 may be coupled to the processor 110 and may store the captured information. The process engine 106 may facilitate to determine a space risk profile associated with the space and a person risk profile associated with the person. The space risk profile and the person risk profile may indicate an extent of the risk associated with the person and the space, respectively. Based on the risk profile, the processor 110 may perform at least one of an automatic identification of a mitigation to reduce the infection risk and an automated generation of an alert. The system 100 may be implemented by way of a single device or a combination of multiple devices that are operatively connected or networked together. The system 100 may be implemented in hardware or a suitable combination of hardware and software.

The system 100 may be a hardware device including the processor 110 executing machine readable program instructions to facilitate dynamic risk assessment. Execution of the machine-readable program instructions by the processor 110 may enable the proposed system to facilitate dynamic risk assessment. The "hardware" may comprise a combination of discrete components, an integrated circuit, an application-specific integrated circuit, a field programmable gate array, a digital signal processor, or other suitable hardware. The "software" may comprise one or more objects, agents, threads, lines of code, subroutines, separate software applications, two or more lines of code or other suitable software structures operating in one or more software applications or on one or more processors. The processor 110 may include, for example, microprocessors, microcomputers, microcontrollers, digital signal processors, central processing units, state machines, logic circuits, and/or any devices that manipulate data or signals based on operational instructions. Among other capabilities, processor 110 may fetch and execute computer-readable instructions in a memory operationally coupled with system 100 for performing tasks such as processing of captured information, input/output processing, extraction, and/or any other functions. Any reference to a task in the present disclosure may refer to an operation being or that may be performed on the captured information.

Figure 2:
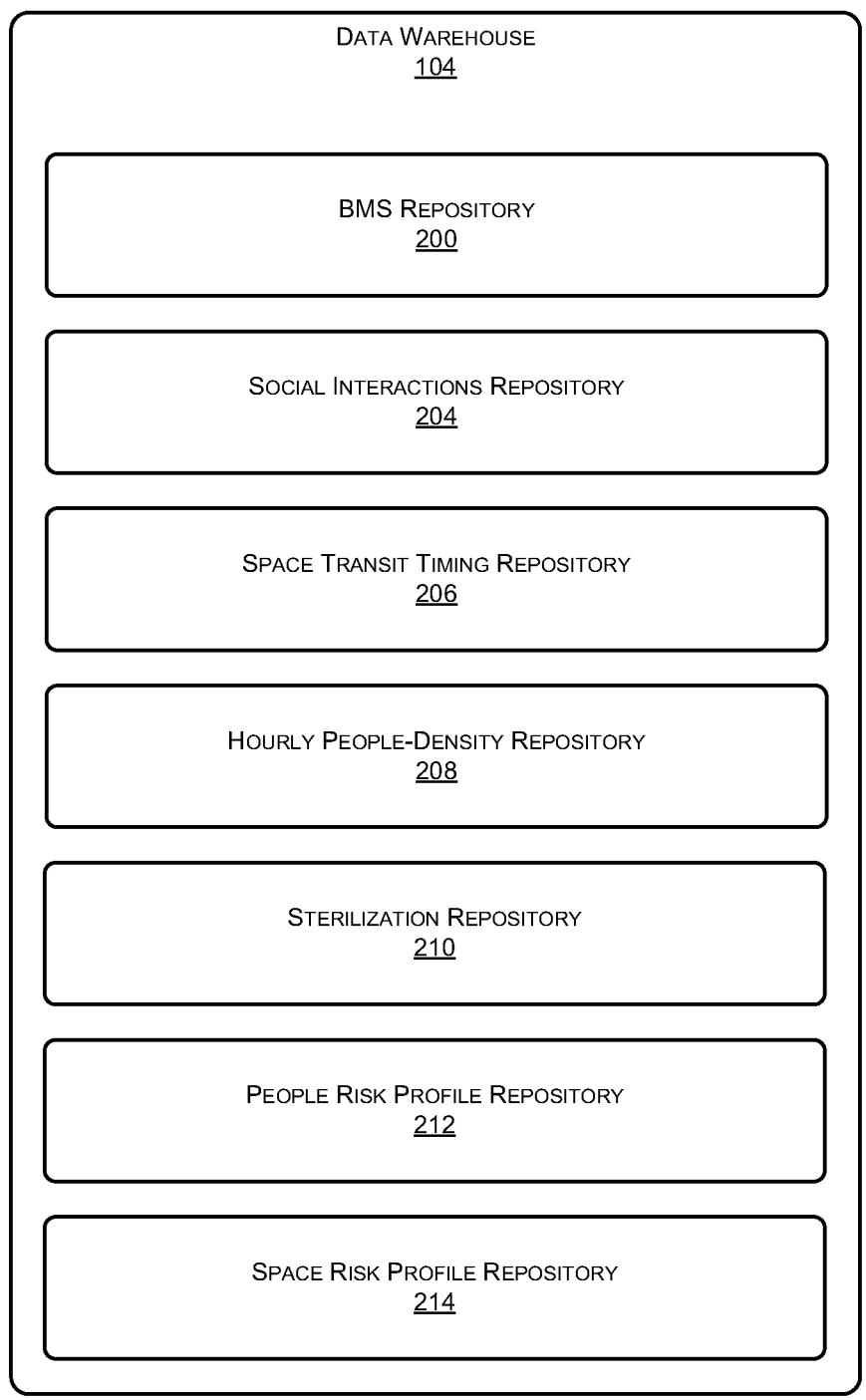
FIG. 2 illustrates a block diagram of a data warehouse of the dynamic risk assessment system of FIG. 1, according to an example embodiment of the present disclosure.

FIG. 2 illustrates a block diagram of a data warehouse of the dynamic risk assessment system of FIG. 1, according to an example embodiment of the present disclosure. As shown in FIG. 2, the data warehouse 104 may include a Building Management System (BMS) repository 200, a social interactions repository 204, a space transit timing repository 206, an hourly people-density repository 208, a sterilization repository 210, a people risk profile repository 212 and a space risk profile repository 214. The BMS repository 200 may be configured to store the building plan data. The social interactions repository 204 may store the interaction data and the network centrality data. The space transit timing repository 206 may store the space transit time data. The hourly people-density repository 208 may store the indoor movement data. The sterilization repository 210 may store the hygiene and behavior data. The people risk profile repository 212 may store the person risk profile. The space risk profile repository 214 may store the space risk profile. Data from these repositories may be used for assessing the risk by the system 100. In an example embodiment, the space risk profile and the person risk profile may be automatically updated in the space risk profile repository 214 and the people risk profile repository 212 respectively.

Figure 3:
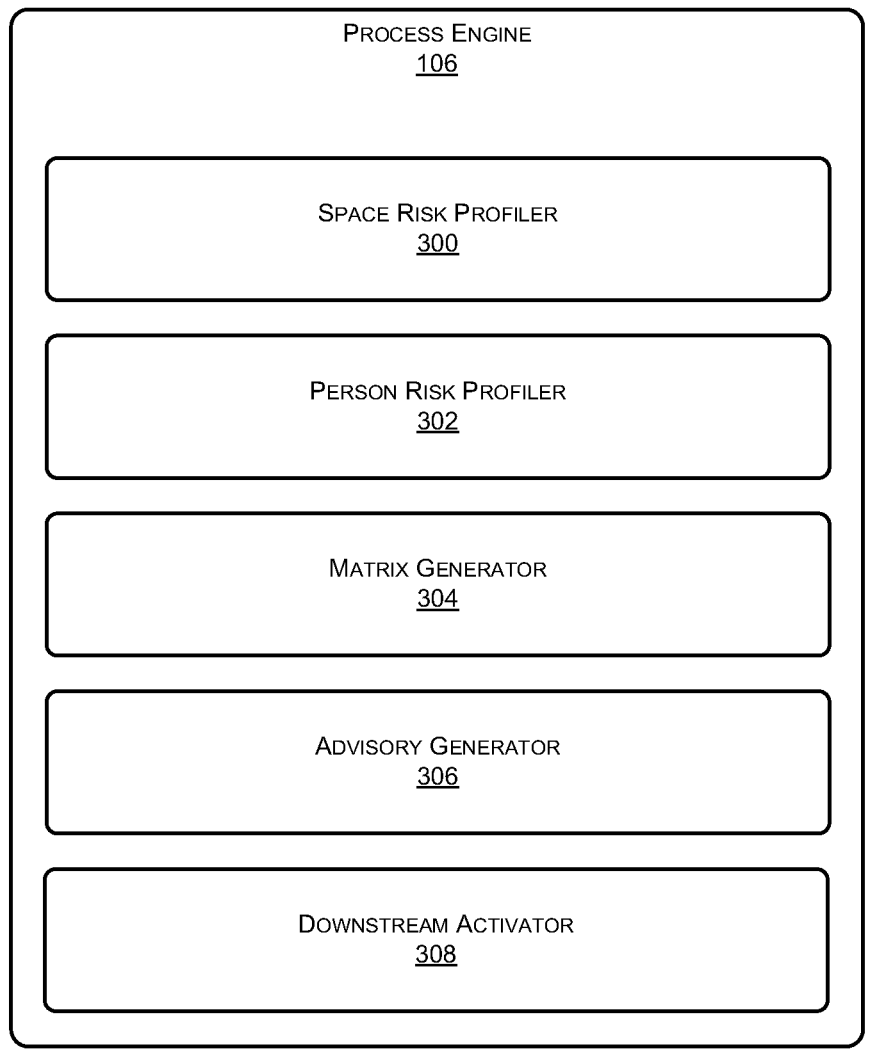
FIG. 3 illustrates a block diagram of a process engine of the dynamic risk assessment system of FIG. 1, according to an example embodiment of the present disclosure.

FIG. 3 illustrates a block diagram of the process engine 106 according to an example embodiment of the present disclosure. In an example embodiment, the process engine 106 may receive the captured information directly from the data capturer 102. In another example embodiment, the process engine 106 may receive the captured information in the form of stored data from the data warehouse 104. The process engine 106 may assess the interactions to identify risks associated with people and/or space. As shown in FIG. 3, the process engine 106 may include a space risk profiler 300, a person risk profiler 302, a matrix generator 304, an advisory generator 306, and a downstream activator 308. The process engine 106 may determine a risk score associated with the infection risk corresponding to the plurality of data elements. In an example embodiment, the risk score may include a space risk score corresponding to the space and a person risk score associated with the person. The risk score can be a weighted function of the corresponding risk factors associated with the space and/or the person. Using the space risk profiler 300 and based on the space risk score, the process engine 106 may determine the space risk profile associated with the space. Similarly using the person risk profiler 302 and based on the person risk score, the process engine 106 may determine the person risk profile associated with the person. The process engine 106 may be coupled to the data warehouse 104 to automatically update the space risk profile and the person risk profile. The space risk profiler 300 and the person risk profiler 302 may automatically update the space risk profile and the person risk profile in the space risk profile repository 214 and the people risk profile repository 212 respectively. Based on the risk profile, the processor performs at least one of an automatic identification of a mitigation to reduce the infection risk and an automated generation of an alert. The output device 108, coupled to the processor, may facilitate to generate, based on the identified mitigation, a personalized advisory trigger to reduce the risk factors associated with the plurality of data elements. Upon receipt of the personalized advisory trigger from the output device 108, the advisory 1s generator 306 may generate a personalized advisory. The downstream activator 308 provide actions to minimize the risk upon receipt of the identified mitigation. In an example embodiment, the matrix generator 304 may receive a label associated with the space risk profile and the person risk profile. Depending on the label, the matrix generator 304 assesses the risk by generating at least one of a person risk vector, a space risk vector, a person-person risk matrix, and a person-space risk matrix.

Figure 4:
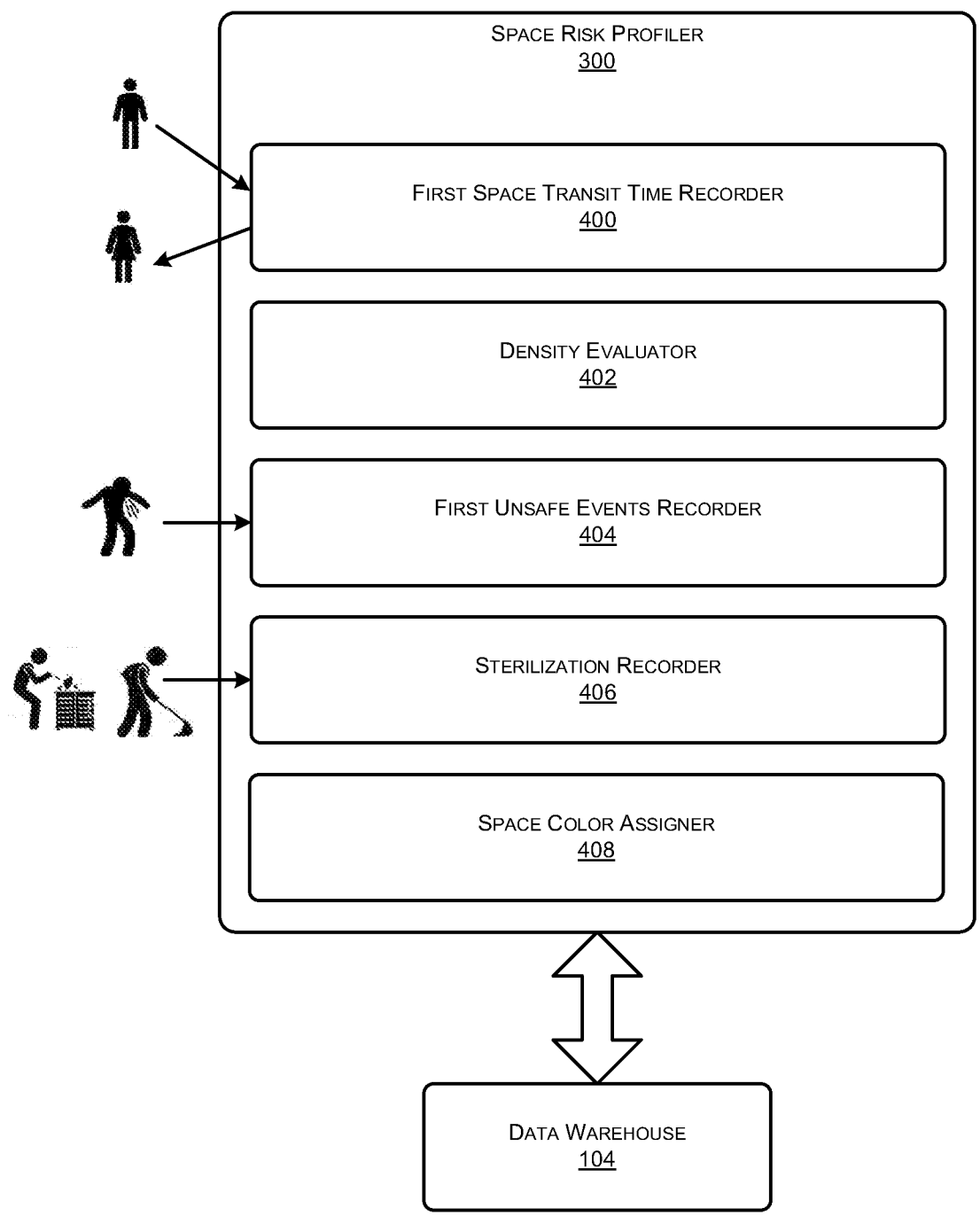
FIG. 4 illustrates a block diagram of a space risk profiler of the process engine of FIG. 3, according to an example embodiment of the present disclosure.

FIG. 4 illustrates a block diagram of the space risk profiler 300, according to an example embodiment of the present disclosure. In an example embodiment, the space risk profiler 300 is coupled to the data warehouse 104. The space risk profiler 300 may include a first space transit time recorder 400, a density evaluator 402, a first unsafe events recorder 404, a sterilization recorder 406, and a space color assigner 408. The first space transit time recorder 400 may be triggered when the person performs an action including at least one of entering the space and exiting the space. The action may be sensed or captured by the data capturer 102. Considering an example wherein the space is a meeting room from an employee's workplace. When the employee enters the meeting room, the first space transit time recorder 400 may be triggered, and the system may store the corresponding information. The captured information may relate to, for example, an identity of the space (Place ID) corresponding to the meeting room, an identity of the person (Person ID of the employee), entry time i.e. the time when the person entered the space, exit time, i.e. the time when the person exits the space, and other such information. The corresponding information may be stored in the space transit timings repository 206 of the data warehouse 104. The density evaluator 402 may interact with the space transit timings repository to periodically evaluate a density of the persons in the space. Upon evaluation of the density, the density evaluator 402 may store a space identity information in the hourly people-density repository 208 of the data warehouse 104. The space identity may be associated with the space and may account for an average number of the persons entering or exiting the space in a predefined time interval. In an example embodiment, the density evaluator 402 may be scheduled to periodically evaluate density of people/space, for example, on an hourly basis. The first unsafe events recorder 404 may be triggered upon detection of a first pre-defined unsafe event in the space. The system 100 may include a list of events categorized as potentially unsafe events (pre-defined unsafe event). In an example embodiment, the first pre-defined unsafe event may pertain to non-compliance of a safety measure. In an example embodiment, the first unsafe events recorder 404 may be coupled with the CCTV or BLE sensors of the data capturer 102 to capture occurrence of the first pre-defined unsafe event. For example, if a person without a mask sneezes in the meeting room, the first unsafe events recorder 404 may provide an interrupt to the space color assigner 408. The interrupt may notify the space color assigner 408 to assign red/amber color to the space (meeting room) depending on severity. It may be appreciated that other such notification and examples are also possible wherein various other risk alert symbols or identifiers may be used. The sterilization recorder 406 may be triggered upon detection of a sterilization event pertaining to the space. The sterilization recorder 406 may be coupled with the CCTV or BLE sensors of the data capturer 102 to detect the occurrence of the sterilization event.

In an example embodiment, the space risk profiler 300 may analyze, for example, an activity in a given space, sterilization actions and people transit details stored in the data warehouse 104. Based on the analyzed activity, the space risk profiler 300 may assign risk identification symbols or colors such as, for example, red (R), orange (O), yellow (Y), or green (G) to the space. In an example embodiment, the risk identification symbols and/or colors may be assigned temporally and may be updated frequently. In an example embodiment, the space risk profiler 300 may include a space color assigner 408 to assign a color based indication depending on the space risk profile. The color based indication indicates an extent of a safety or the infection risk pertaining to the space. In an example embodiment, in order to assign the risk profile to the space, the space color assigner 408 may cooperate or interact with at least one of the space transit timings repository 206, the hourly people-density repository 208, the people risk profile repository 212, the BMS repository 200 and the sterilization repository 210. The space color assigner 408 may then assign a color thereby assigning a risk profile to the space. The assigned color, along with other details, such as, for example, the place ID, entry time of the person in the space and exit time of the person may be stored in the space risk profile repository 214.

In an example embodiment, the color based indication may be generated by the space color assigner 408, as per a first schedule, and by an interaction with the at least one repository. The interaction may be with the space transit timings repository 206 to assign a first score; with the people risk profile repository 212 to assign a second score; with the hourly based density repository 208 to assign a third score; with the BMS repository 200; and with the sterilization repository 210 to assign a fifth score. In an embodiment, the process engine 106 may compute an average of the first score, the second score, the third score, the fourth score and the fifth score to generate a first average weighted score. In an example embodiment, the space risk profiler 300 may use the respective score for various activities and temporal data to assign the right color to the space. In an example embodiment, the temporal data may be obtained by capturing multiple snapshots of the data at various points in time 't', in order to monitor if a situation is improving, degrading, or staying constant with time. In an example, the severity score may be a weighted function of relevant parameters. For example, the parameters, such as cleaning activity in a space, or ventilation may have influence on weights that can be pre-configured. A higher weight value may imply a higher risk. In an example, techniques based on conditional probability ideas can also be may also be employed, wherein a risk of a given situation A may affect severity score value of a situation B as compared to a case where the situation B is looked at separately in isolation. In an example embodiment, based on the first average weighted score and a first set of pre-defined rules, the rules engine 112 of the processor 110 may assign a predefined color pertaining to the color based indication. Once the predefined color is assigned to a space, the space risk profile repository 214 of the data warehouse 104 may be updated. The first set of pre-defined rules may correspond to one or more predefined thresholds that may decide the nature of the assigned predefined color pertaining to the color based indication. In an example embodiment, multiple predefined thresholds may be set based on equal distribution of limits pertaining to the multiple predefined thresholds. In an example embodiment, the first average weighted score may be computed based on respective weight assigned to each interaction. In an example embodiment, the respective weight may be assigned by a first model of the space risk profiler 300. For example, the first model may be a linear regression model that is trained based on machine learning. In an example embodiment, the first model of the space risk profiler 300 may assign respective weights. Based on the assigned weights and the respective scores (say, for example, score A1, A2, A3, A4, A5), the first average weighted score may be computed. In an example embodiment, the first average weighted score may be calculated as =(A1×W1+A2× W2+A3×W3+A4×W4+A5×W5). In an example, each weight may be assigned a value such that total sum of all weights (W1 to W5) may be equal to 1. For example, the weights may have a value of W1=0.1, W2=0.3, W3=0.2, W4=0.1, W5=0.3. In an example embodiment, initial value of the weights may be assigned based on personalized recommendations (cold started typical weight values). The weights can be assigned eventually by machine learning using linear regression model. The model may be trained over a period of time to increase accuracy for estimation of weights and/or scores. Various criterion may be considered for training the model, based on the requirements. For example, for a total score (or a maximum score) of 10, the multiple predefined thresholds may be set as a first threshold for a score below 3.4, a second threshold for a score between 3.4 to 6.7 and a third threshold for a score above 6.7 to 10. In this example, the predefined color pertaining to the color based indication may be, for example, green color if the first average weighted score is below the first threshold, amber color if the first average weighted score lies within the range of the second threshold, and red color if the first average weighted score is above the value of the third threshold. The present disclosure may not be limited by the mentioned predefined thresholds/color based indication and various other threshold and corresponding colors may be assigned. The assigned color is used to identify risk profile of the space. In an example embodiment, when a sterilization event is detected, the sterilization recorder 406 provides the interrupt to the space color assigner 408 to assign a default minimum color to the space. For example, certain space or areas may be riskier by nature than others. In this case, the default minimum color of these areas, such as restrooms and pantries may be, for example, amber, while for other places the default minimum color may be, for example, green. The sterilization recorder 406 may also store the place ID and last sterilized time in the sterilization repository 210 of the data warehouse 104. In an example embodiment, once evaluation of risk and appropriate risk mitigation is performed, the system may facilitate automated and/or manual closure of the detected event. The system may also facilitate feedback based learning of the first model associated with the space risk profiler 300 to allow an automated update of the first set of pre-defined rules and/or adjustment of the predefined threshold. The feedback associated with the feedback based learning may be automated or manual.

Figure 5:
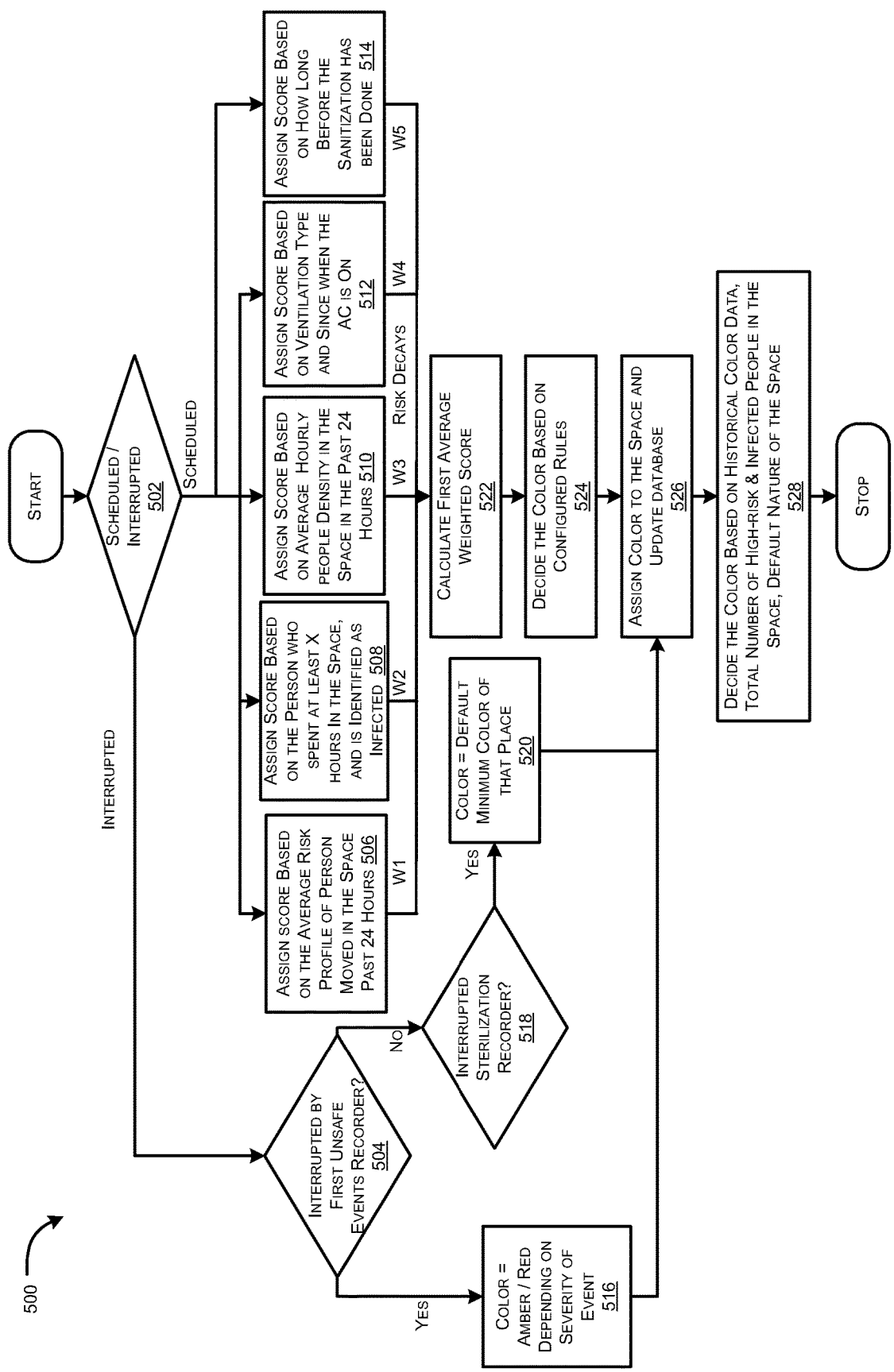
FIG. 5 illustrates a flow diagram of a method assigning a color to a space, according to an example embodiment of the present disclosure.

FIG. 5 illustrates a flow diagram of a method 500 of the space color assigner 408 for assigning a color to a space, according to an example embodiment of the present disclosure. At 502, the method 500 may initiate by checking if the space color assigner 408 is scheduled or interrupted (i.e. receipt of an interrupt) to assign the color to a space. Upon confirming receipt of an interrupt, at 504, it may be checked if the interrupt may be received from the first unsafe events recorder 404. At 516, upon confirming that the interrupt is received from the first unsafe events recorder 404, the method may proceed by assigning a color to the space. For example, amber/red color may be assigned depending on severity of the event. At 518, upon confirming that the interrupt is not received from the first unsafe events recorder 404, it may be checked if the interrupt may be received from the sterilization recorder 406. If yes, then at 520, the method may proceed by assigning a default minimum color to the space. If the interrupt is not received, the space color assigner 408 is scheduled to assign a color to the space. In an example embodiment, a color based indication may be generated by the space color assigner 408, as per a first schedule, and by an interaction with the at least one repository. At 506, the interaction may be with the space transit timings repository 206 to assign the first score (W1) based on an average risk profile of the person present in the space at a pre-defined time duration. For example, a pre-defined time duration may be, without limitation, 1 hour or 24 hours. At 508, the interaction may be with the people risk profile repository 212 to assign the second score (W2) based on an identification of an infected person from the person in the space. The second score may correspond to a time duration spent by the infected person in the space. At 510, the interaction may be with the hourly people-density repository 208 to assign the third score (W3) based on average hourly density of the persons present in the space for a time period. At 512, the interaction may be with the BMS repository 200 to assign the fourth score (W4) based on predefined attributes. The predefined attributes may include at least one of a ventilation type of the space and time duration for which air conditioning is switched ON in the space. At 514, the interaction may be with the sterilization repository 210 to assign the fifth score (W5) based on an extent of time duration passed after the last sanitization of the space. In an example embodiment, the space risk profiler 300 may use the respective scores for various activities and past temporal data to assign the right color to the space. At 522, the process engine 106 (or the space risk profiler) may compute an average of the first score (W1), the second score (W2), the third score (W3), the fourth score (W4) and the fifth score (W5) to generate a first average weighted score. In an example embodiment, the risk decays may also be considered, while assigning the weights or while generating the first average weighted score. For example, a lack of activity may lead to decay of the risk, even for a space with high infection risk. For example, if it may have been 6 hours passed since a space was overcrowded, a score of 10 (out of 10) may be assigned. Further, if it may have been 6 to 12 hours passed since a space was overcrowded, a score of 7.5 (out of 10) may be assigned). If it may have been 12 to 18 hours passed since the space was overcrowded, a score of 5 (out of 10) may be assigned. Further, it may have been 18 to 24 hours passed since the space was overcrowded, a score of 2.5 (out of 10) may be assigned and if it may have been more than 24 hours passed since the space was overcrowded, a score of 0 (out of 10) may be assigned. Various such rules/criteria may be predefined for automated assignment of weights and scores by the system. At 524, based on the first average weighted score and a first set of pre-defined rules, the rules engine 112 of the processor 110 may assign a predefined color pertaining to the color based indication associated with the space. The first average weighted score may be computed by assigning different value of weights to each of the scores (W1 to W5). For example, the second score (W2) that corresponds to infection and the fifth score (W5) that corresponds to sanitization may have more impact in increasing or reducing the infection risk respectively and hence may carry more weightage. In an example, a weight of 0.3 each may be assigned to W2 and W5. In an example, the first score W1 corresponding to average risk profile of people and fourth score W4 corresponding to ventilation may carry relatively lesser weightage so a weight of 0.1 each may be assigned. In another example, the risk decay may also carry less weightage, so a weight of 0.2 may be assigned. The assignment of respective weights may vary based on the space requirements and/or situational basis. In an example embodiment, the space color assigner 408 may include a model that may be trained and updated based on various situation based rules for automated assignment of weights based on the different situations/scenarios. The color based indication may be updated in the space risk profile repository 214 of the data warehouse at predefined time intervals. In an example embodiment, at 528, a subsequent schedule to the first schedule may be assigned. The subsequent schedule for assigning the color pertaining to the color based indication may be dependent on historical color data, total number of high-risk persons and infected persons in the space and a default nature of the space. This means that past data, total number of high-risk/infected people and default nature of a space/place may be used to decide how frequently the space color assigner 408 assigns a color to the space. In an example embodiment, the first set of pre-defined rules (or predetermined rules) include conditions to activate color based indication pertaining to the risk. For example, if the first average weighted score (or weighted score) is greater than seven, then the color may be selected as Red (R). In the same example or a different example, if the first average weighted score is less than three (3) then the color may be selected as green (G). It may be appreciated that the ranges for the first average weighted score weighted score and corresponding colors may be provided for purposes of example only and these ranges and corresponding colors may be configurable.

The person risk profiler 302 identifies risk profile of a person. The person risk profiler 302 facilitates to determine the person risk profile associated with the person based on the person risk score. The person risk profiler 302 analyzes a person's behavior, attire, and interactions stored in the data warehouse 104. Based on the analyzed aspects, a temporal risk color such as, for example, red, orange, yellow or green, and other such colors may be assigned to the person depending on the risk. The risk color may change temporally based on a severity of input data and past temporal data. The person risk profiler 302 also performs social interaction analysis between the persons (network-centrality data) that is stored in the data warehouse 104. This may be done to identify metrics such as network-centrality in network or how socially active a person is in the network or a given environment.

Figure 6:
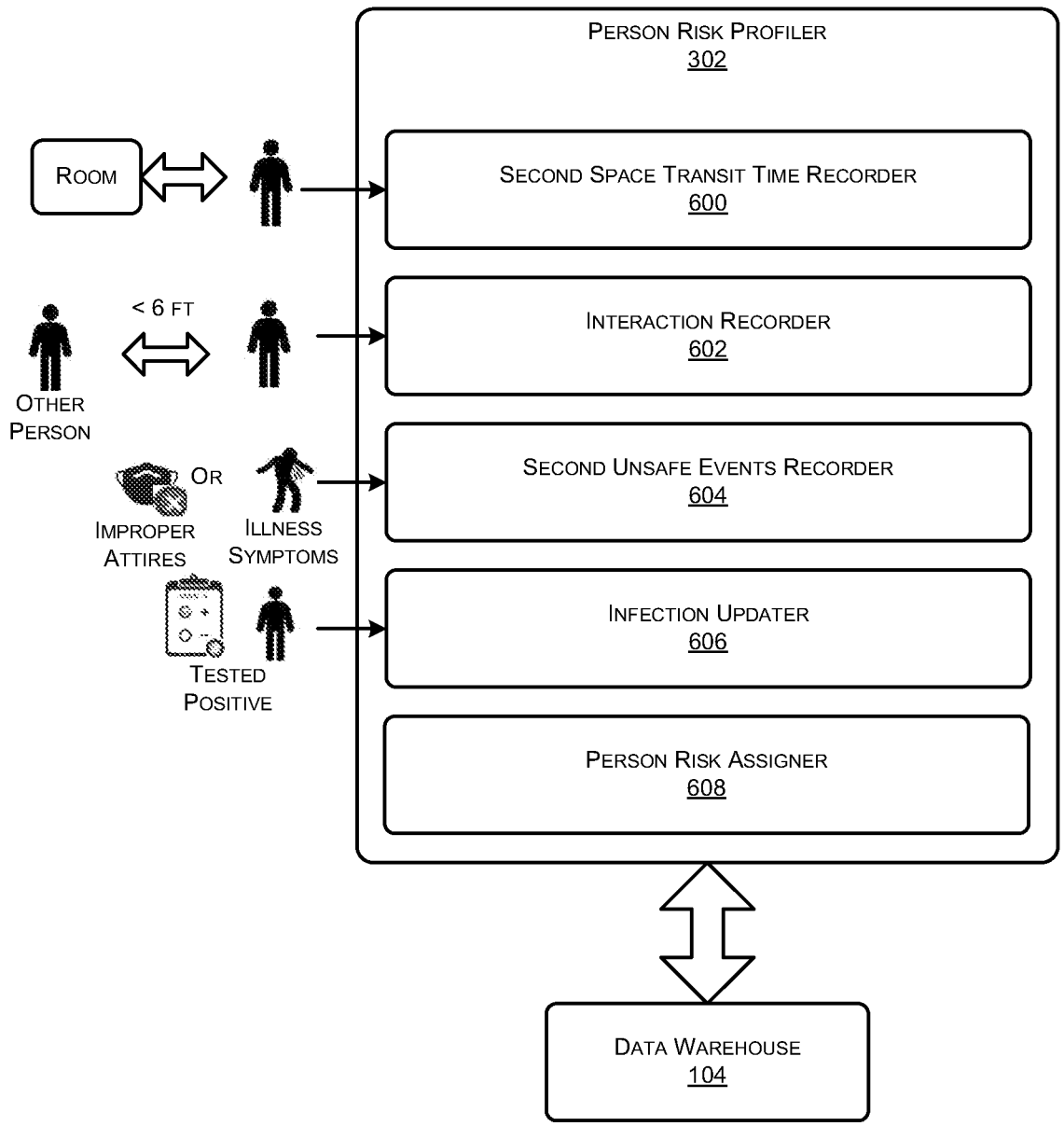
FIG. 6 illustrates a block diagram of a person risk profiler disclosed in the process engine of FIG. 3, according to an example embodiment of the present disclosure.

FIG. 6 illustrates a block diagram of the person risk profiler 302, according to an example embodiment of the present disclosure. In an example embodiment, the person risk profiler 302 may be coupled to the data warehouse 104. The person risk profiler 302 may include a second space transit time recorder 600, an interaction recorder 602, a second unsafe events recorder 604, an infection updater 606, and a person risk assigner 608. The second space transit time recorder 600 is triggered when the person performs an action. The action may include at least one of entering the space and exiting the space. The action may be sensed or captured by the data capturer 102. For example, if the space is a meeting room of a workplace and the person is an employee. When the employee may enter the meeting room, the second space transit time recorder 600 may be triggered. Subsequently, the system may store the corresponding information (collected by data capturer 102) in the space transit timings repository 206 of the data warehouse 104. The information may relate to, for example, an identity of the space (Place ID) corresponding to the meeting room, an identity of the person (Person ID of the employee), entry time i.e. the time when the person entered the space, exit time, i.e. the time when the person exits the space, and other such information. The interaction recorder 602 may be triggered when a distance between two persons crosses a predefined threshold distance, wherein at least one of the two persons may be identified to include corresponding high risk profile. For example, if the predefined threshold distance is 6 feet and when one person stands at less than 6 feet distance from the other the person whose risk profile is being evaluated as high risk or is being identified, the interaction recorder 602 may be triggered. The closeness in distance between the 2 persons may be sensed or captured by the data capturer 102. As an example, the BLE sensors from the data capturer 102 may detect the closeness. The interactions recorder 602 store person ID, ID of persons with whom interaction may have occurred, the entry-time, the exit-time, and an interaction risk (low, medium, high) to the people-people interactions repository 204 of the data warehouse 104. The risk score may take into account an interaction risk that depends on various parameters. For example, the parameters may include a distance between the two persons, whether the persons are wearing masks, presence of ventilation in the space where the persons met, whether AC was ON in the space and other such parameters. The second unsafe events recorder 604 may be triggered, upon detection of a second pre-defined unsafe event pertaining to the person. The second pre-defined unsafe event pertains to non-compliance of at least one safety measure by the person. The second unsafe events recorder 604 may be coupled to the CCTV or BLE sensors of the data capturer 102 to capture occurrence of the second pre-defined unsafe event. In an example embodiment, upon detection of the second pre-defined unsafe event, the second unsafe events recorder 604 may send a first interrupt signal. For example, if a person without a mask sneezes in the meeting room or if a person is not wearing a mask, the second unsafe events recorder 604 may send the first interrupt signal to the person risk assigner 608. The first interrupt signal is to notify the person risk assigner 608 of at least one of a medium risk profile and a high risk profile of the person associated with the second pre-defined unsafe event. The type of risk may depend on severity of the second pre-defined unsafe event. In another example embodiment, upon detection of the infected person, the infection updater 606 may be updated and may send a second interrupt signal to the person risk assigner 608. For example, the infection updater 606 is updated by the system 100 when a person is infected and/or tested positive for an infection. The second interrupt signal is to update the person risk profile and to raise a flag indicating a high infection risk due to the person. In an example embodiment, an external device like a smart phone or a computer may be used to update infection data of a person.

In an example embodiment, the person risk assigner 608 may assign the person risk profile to the person as per a second schedule. The person risk profile may be assigned by an interaction of the person risk assigner 608 with the at least one repository. The repository may be at least one of the space transit timings repository 206, the space risk profile repository 214, the people risk profile repository 212, and the people-people interactions repository 204. The person risk assigner 608 then assigns a risk profile (low, medium, high) to the person. The assigned risk profile, along with the Person ID, and infection data is stored in the people risk profile repository 212.

Figure 7:
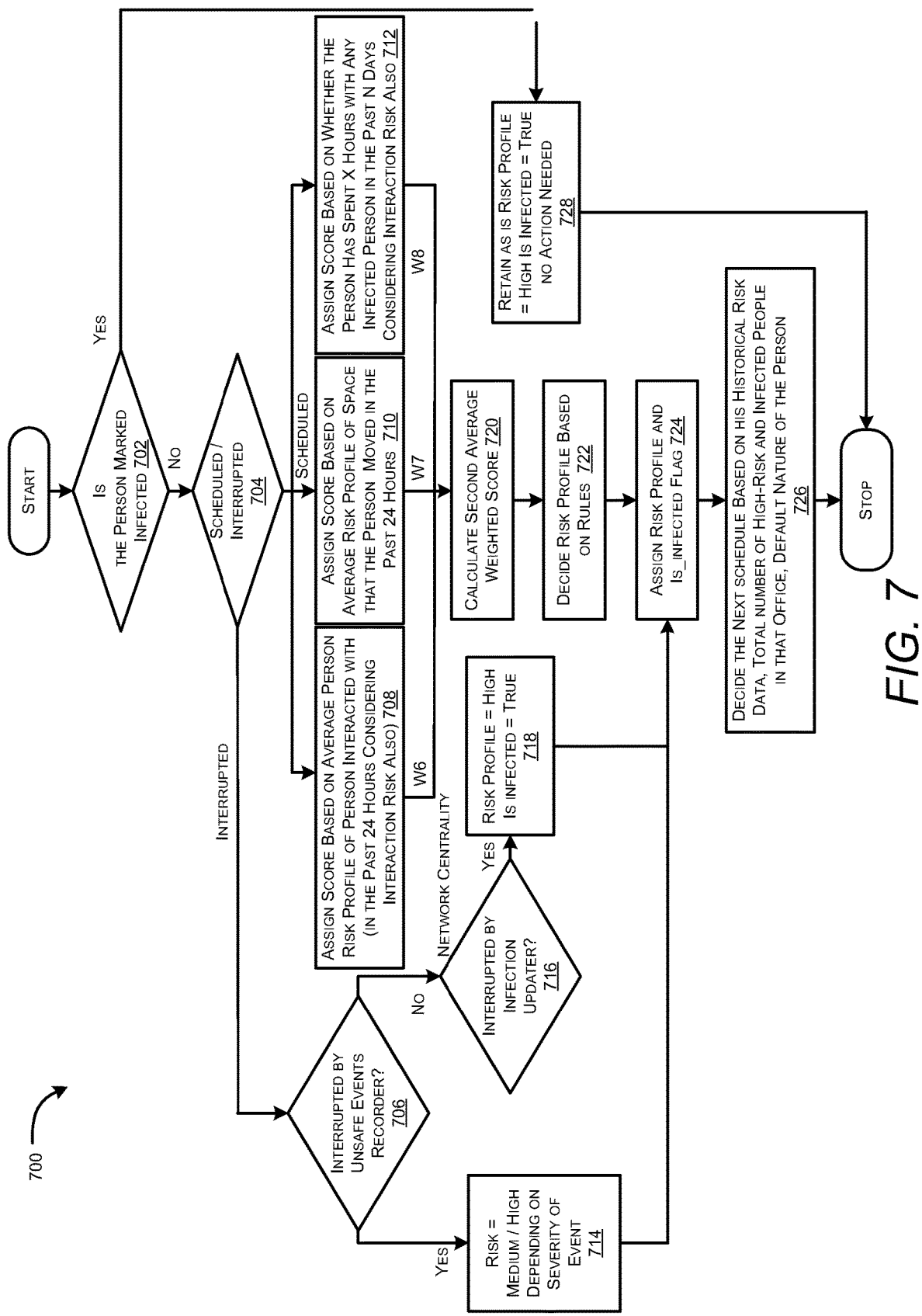
FIG. 7 illustrates a flow diagram of a method of assigning a risk profile to a person, according to an example embodiment of the present disclosure.

FIG. 7 illustrates a flow diagram of a method 700 of the person risk assigner 608 for assigning a risk profile to a person, according to an example embodiment of the present disclosure. At 702, the method 700 may initiate by checking if a person is already marked as infected. If the person is marked as infected, the method 700 may proceed by retaining the person's high risk profile as shown in 728. If the person is not marked as infected, the method 700 may proceed by checking if the person risk assigner 608 is scheduled or interrupted (i.e. receipt of an interrupt) to assign the profile to the person if an interrupt is received. Upon confirming receipt of an interrupt, at 704, it may be checked if the interrupt may be received from the second unsafe events recorder 604. If yes, the system may proceed by assigning a risk profile to the person. For example, at 714, the person risk assigner 608 may assign a medium or a high risk to the person, depending on severity of the event. Upon confirming that the interrupt is not received from the second unsafe events recorder 604, the system may confirm if the interrupt is received from the infection updater 606. If yes, then at 718, the method may proceed by assigning a high risk to the person and marking the person as infected. for example, amber/red color depending on severity of the event. At 704, upon confirming that the interrupt is not received, and the person risk assigner 608 may be scheduled to assign the person risk profile to the person. The person risk assigner 608 may assign the person risk profile to the person as per a second schedule. The person risk profile may be assigned by an interaction with the at least one repository. At 708, the interaction may be with the people risk profile repository 212 to assign a sixth score (W6). The sixth score may be assigned based on an average risk profile of the person interacting with another person in a pre-defined time duration. For example, as shown in 708, the sixth score is assigned considering the interaction risk and based on an average risk profile of persons that interacted with a potentially infected person/infected person in the past 24 hours. At 710, the interaction may be with the space transit timings repository 206 to assign a seventh score (W7). The seventh score may be assigned based on an average risk profile of the space where the person physically enters or exits the space in a pre-defined time duration. For example, as shown in 710, the seventh score may be assigned based on the average risk profile of spaces that the person visited in the past 24 hours. At 712, the interaction may be with the social interactions repository 204 to assign an eighth score (W8). The eight score may be assigned based on time duration spent by persons with the potentially infected person/infected person. For example, as shown in 712, the eighth score may be assigned considering interaction risk and based on whether the person has spent X hours with any infected person in past N days. At 720, the process engine 106 (or the processor) may compute an average of the sixth score, the seventh score and the eighth score to generate a second average weighted score. At 722, based on the second average weighted score and a second set of pre-defined rules, and by using the rules engine 112 of the processor 110, the person risk assigner 608 assigns the person risk profile to the person. The second average weighted score may be based on respective weight assigned to each interaction. In an example embodiment, the respective weight may be assigned by a second model of the person risk profiler 302. For example, the second model may be a linear regression model that may be trained by machine learning (ML). In an example embodiment, the person risk profiler 302 may assign respective weights (W6, W7, W8) using the second model and obtain respective scores (say, for example, score B1, B2, B3) and the second average weighted score. In an example embodiment, the second weighted score may be calculated as $=(B1 \times W6 + B2 \times W7 + B3 \times W8)$. In an example, each weight may be assigned a value such that total sum of all weights (W6, W7, W8) may be equal to 1. For example, the weights may have a value of W6=0.2, W7=0.2, W8=0.6. In an example embodiment, initial value of the weights may be assigned based on personalized recommendations (cold started typical weight values) and the weights can be assigned eventually by machine learning using linear regression model. The model may be trained over a period of time to increase accuracy for estimation of weights and/or scores. Various criterion may be considered for training the model, based on the requirements. The second set of pre-defined rules may correspond to one or more predefined thresholds that may decide the nature of the person risk profile and/or a color may be assigned based on the predefined thresholds. In an example embodiment, the multiple predefined thresholds may be set based on equal distribution of limits pertaining to the multiple predefined thresholds. For example, for a total score (or a maximum score) of 10, the multiple predefined thresholds may be set as a first threshold for a score below 3.4, a second threshold for a score between 3.4 to 6.7 and a third threshold for a score above 6.7 to 10. In this example, the color corresponding to the person risk profile may be, for example, green color if the second average weighted score is below the first threshold, amber color if the second average weighted score lies within the range of the second threshold, and red color if the second average weighted score is above the value of third threshold. The present disclosure may not be limited by the mentioned predefined thresholds/color based indication and various other threshold and/or corresponding colors may be assigned. In an example embodiment, once evaluation of the risk and appropriate risk mitigation may be performed, the system may facilitate automated and/or manual closure of the detected event. The system may also facilitate feedback based learning of the second model associated with the person risk profiler 302 to allow an automated update of the second set of pre-defined rules and/or adjustment of the predefined threshold. The feedback associated with the feedback based learning may be automated or manual. At 724, either based on the interrupt (714, 718) or based on the second schedule as explained hereinabove, the person risk profiler 302 may facilitate assigning the person risk profile and raising a flag indicating a high infection risk. Once the person risk profile is assigned to the person, the person risk profile repository 212 of the data warehouse 104 may be updated. In an example embodiment, the processor may determine a subsequent schedule to the second schedule based on at least one of a historical risk data, total number of high-risk profile of persons in the space and a default nature of the person. In an example embodiment, historical data, total number of high-risk/infected people and default nature of a person may facilitate to decide how frequently the person risk assigner 608 assigns the person risk profile to the person.

In an example embodiment, the space risk profiler 300 may assign default minimum color such as, for example, green color to a normal space, and orange to a risk prone space (like restroom). If a person and the space both are assigned a green color, and if the person does an unsafe behavior, the person is marked red by the person risk profiler 302 and the space may be marked with a color, for example, yellow color by the space risk profiler 300. In an example, if a space with yellow color (i.e. moderate risk profile) may be mopped by a cleaner, the space may be assigned a green color (i.e., normal/low risk profile). In another example, if a person may work in a room without a proper gear (like a face mask), the person and space both may be marked red by the person risk profiler 302 and space risk profiler 300 respectively. In yet another example, if there may be no activity in a room with high risk profile for 24 hours, the risk may be considered to decay and the room may be assigned a green color. In yet another example, if a space such as a meeting room is well ventilated, the space color may remain green even after a meeting is conducted in that room. In yet another example, if a crowded team meeting is carried out in an air conditioned room, the room may be assigned an orange color.

In reference to FIG. 3, the matrix generator 304 is coupled to the space risk profiler 300 and the person risk profiler 302 to receive the assigned colors or any other indication pertaining to the space and the person, respectively. Based on the assigned colors/indication, the matrix generator 304 may generate the interaction risk matrix including a person risk vector, a space risk vector, a person-person risk matrix and a person-space risk matrix to assess risk. For example, a Red person (high risk person) wearing a protective gear and entering a Green (safe) space will still be Green interaction risk. Example matrices are illustrated in TABLE 3 below, wherein R refers to red, G refers to green and Y refers to yellow.

TABLE 3

| Person Risk (t) | | Space Risk (t) | |
|---|---|---|---|
| P1 | R | S1 | G |
| P2 | G | S2 | Y |
| P3 | Y | S3 | G |
| ... | | ... | |
| ... | | ... | |
| Pn | G | Sn | R |

| Person-Person Sparse Matrix (t) | | | | | |
|---|---|---|---|---|---|
| | P1 | P2 | P3 | ... ... | Pn |
| P1 | R | R | R | | R |
| P2 | R | G | G | | G |
| P3 | R | Y | Y | | Y |
| ... | | | | | |
| ... | | | | | |
| Pn | R | G | Y | | G |

| Person-Person Sparse Matrix (t) | | | | | |
|---|---|---|---|---|---|
| | S1 | S2 | S3 | ... ... | Sn |
| S1 | R | R | R | | R |
| S2 | G | G | G | | R |
| S3 | Y | Y | Y | | R |
| ... | | | | | |
| ... | | | | | |
| Sn | G | Y | G | | R |

In an example embodiment, the matrix generator 304 may use Naïve Bayes conditional probability to generate and update risk metrics for persons and spaces based on previously generated metrics. The generation and update of the risk metrics is mainly done for representing and evaluating the interaction relationship matrix (as exemplified above) for fetching data for fine-grained queries. In an example embodiment, the matrix generator may include a model that may be trained and continuously updated with the interaction relationship matrix so that the model can consider all type of interactions (person-space, and person-person) for accurate computation of the space profile and/or the person profile in the next iteration or schedule. In an embodiment, the risk scores pertaining to the person and the risk may be combined to generate conditional interaction risks. The advisory generator 306 may generate a personalized advisory for workers in a workplace based on desired behaviors. The downstream activator 308 may provide these suggestions to the output device 108. For example, it may happen that a person is at high risk and still does not adhere to wearing mask all the time in an enclosed space. In this case, the data capturer 102 may capture such information and the advisory generator 306 may identify this behavior based on a generated matrix. In return, the advisory generator 306 may provide a signal to the downstream activator 308 to work schedule of that person, to minimize the risk. In an embodiment, the advisory generator 306 and the downstream activator 308 may be rule-based components, wherein specific tasks of the advisory generator 306 and the downstream activator 308 may be based on one or more pre-configured rules. In an example embodiment, the one or more pre-configured rules may be based on an evaluation that depends on at least one of the person risk profile and the space risk profile crossing a predefined threshold point. In an example embodiment, the downstream activator 308 may activate actions such as changing people's schedules to decrease risk, pre-ordering masks, and blocking temporary access to frequently erring individuals. Behavioral group change can also be facilitated by means of a digital nudge or some form of gamification using the downstream activator 308. In an example embodiment, the downstream activator 308 may include an activity actuator, an incentive provider, a digital nudger and a proactive alerter. The activity actuator may enable the downstream activator 308 to provide triggers for certain actions. For example, if an infectious person has moved into a room, the space risk profiler 300 identifies that room to be at significantly-high risk (assigned color 'red'). In this scenario, the activity actuator can send a trigger via the output device 108 to an external BMS system to lock the door from outside, disabling everyone from entering that room. If a person has been tested positive for an infectious disease and identified by the person risk profiler 302 to be of significantly high risk, the activity actuator can send a trigger via the output device 108 to block the person's access card thereby denying him/her access to any rooms, except for moving out of premise, i.e., only one-way access—disabling all inward movement. If sanitization is due to carried out at a place beyond a certain threshold time-period, and the space risk profiler 300 identifies that place to be at moderately-high risk, the activity actuator can send a trigger. The trigger may be sent via the output device 108 to an external BMS system. The trigger may be sent to switch the air conditioning from inside circulation to outside circulation, to switch off the air conditioning beyond a threshold and open up windows automatically. If people density of a room crosses a threshold value and the space risk profiler 300 identifies that room to be at moderately-high risk. In this situation, the activity actuator can send a trigger via the output device 108 to an external BMS system to lock the door from outside. This action may disable anyone from entering that room, till the people exit and the people-density falls below a threshold. If the system 100 identifies that the number of infectious people in an entire premise exceeded a certain threshold value, the activity actuator can send a trigger. The trigger may be sent via the output device 108 to an external BMS system to announce for immediate evacuation. This may lead to lift door locks up thereby forcing people to use stairs while maintaining a social-distance. In an example embodiment, if the system 100 identifies a particular space to be green continuously over a threshold period of time, the incentive provider can send a trigger. The trigger may be sent via the output device 108 to an external gamifying system to provide certain incentives to all the employees of that bay for maintaining good safety and hygiene behavior. If the first unsafe events recorder 404 and/or the second unsafe events recorder 604 identifies an unsafe event (for example, if a person washing hands for less than 20 seconds), the digital nudger with the help of the output device 108 can nudge the person to follow safety standards. For example, the digital nudger may provide a signal to an electronic gadget such as, for example, a wearable band on the person's hand which can in turn vibrate to alert the person about the unsafe event. Alternatively, an LED panel on top of a door can turn red and notify the person about desired action to be taken. If the system 100 identifies that a safe person. i.e., a person with low risk profile, is trying to enter a red space, the proactive alerter can send a trigger. The trigger may be sent via the output device to an external BMS system to activate a buzzer to alarm the person from entering that area. Alternatively, an LED panel in that space can turn red along with a desired warning message. All such triggers, warning and nudges from the downstream activator 308 via the output device 108 enable comprehensive alerting and help in mitigating risks dynamically. In an example embodiment, the system 100 of the present disclosure may sense/detect signals in time stamped people movements, behaviors and their x, y coordinates. For example, this may include spaces visited by a person in a time window, ventilation and space size from Building Management systems, movement trajectory of a person, 'Stay-in a space' log of a person, list of people who visited a space, interaction between persons, face touching action, hand washing times, attire, masks worn, baseline health score of person, and frequency of coming closer than 2 m to another. In an example embodiment, the system 100 may infer certain actions and act accordingly. For example, the system 100 may infer time stamped social network graphs of people-space touch points and identify "omnis" in network with maximum centrality. The system 100 may also identify where to break network into sub-networks for mitigating risk. The system 100 may also compute probabilistic weighted sum of risk factors for each person and space using inputs. The inputs may include centrality of person, centrality of space, max person density over multiple time windows, number of face touches per person, hand wash duration, proximity person-person, size of the space, digital twin triggers for space-specific threshold violations or red flags. The system 100 may send personalized advisory via SMS to each individual on how they must modify their behavior, and dynamic heat map of full facility for management dashboard.

In an example embodiment, the space risk profiler 300 and the person risk profiler 302 can run any suitable computing platform, such as, for example, cloud computing mode or edge computing mode. In an example, the space risk profiler 300 and the person risk profiler 302 may cooperate with a high fidelity video feed analyzer in the cloud computing mode and a low fidelity video analyzer on the edge computing mode. This facilitates obtaining two variants of the same video analysis resulting in computational optimization. Referring back to FIG. 3, in an example embodiment, the cloud computing mode may be a default mode for the space risk profiler 300 and the person risk profiler 302. In this case, if link speed to cloud is detected to go down with increasing latency (which also heightens the risk impact due to the latency) then processing moves from the cloud computing mode to the edge computing mode. Post the restoration of link speeds or lowering of risk impact, the system may facilitate switching the computing back to the cloud computing mode. A computing control layer may include a cloud link speed detector which detects if the link speed is less than a predetermined value. If the speed in not below the predetermined value, the space risk profiler 300 and the person risk profiler 302 may use the cloud computing mode for assessing interactions. If the speed is lower than the predetermined value, an impact risk evaluator may evaluate an impact based on the captured information. For example, the impact evaluator may use captured information, such as, for example, people density, total number of high risk people and a space activity map (illustrated in TABLE 2 below) as input and may assess for each interaction in each space. If the speed is lower than the predetermined value, an impact risk evaluator evaluates the impact of slow detection of an interaction for each data element. For example, the impact evaluator used people density, total number of high risk people and a space activity map (illustrated in TABLE 2 below) as input and assess for each interaction in each space:

If people density >X and
Number of high risk people >Y and
[space id][time-slot]==HIGH
then Impact is High, else Impact is Low

TABLE 2

| Space Id | Time slot | Activity | Impact on people |
|---|---|---|---|
| 1 | 10-10:30AM | Cooking | High |
| 2 | 11-12pm | Sorting | Low |
| 1 | 10:30-11AM | Packing | High |

If the impact is low, the space risk High profiler 300 and the person risk profiler 302 may use the cloud computing mode for assessing interactions. If the impact is high, an edge processing selects the edge computing mode with suitable edge computing device having capacity greater than a threshold. This in turn may trigger the space risk profiler 300 and the person risk profiler 302 to use edge computing mode, after which small data or edge inferences may be sent to the cloud. In an embodiment, both of the space risk profiler 300 and the person risk profiler 302 may have cloud and edge variants for high and low fidelity video feed analysis, respectively.

Figure 8A:
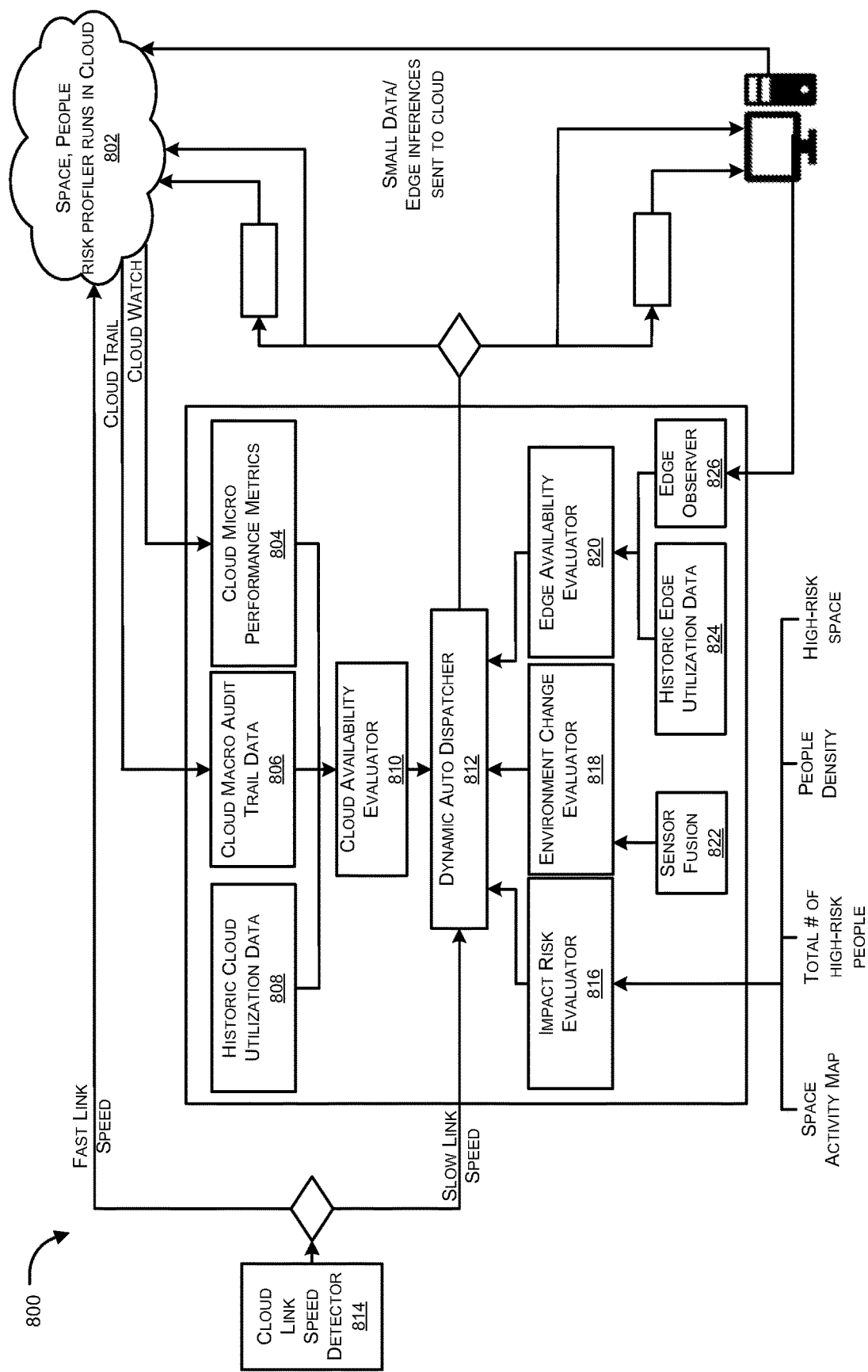
FIG. 8A illustrates a flow diagram showing steps carried out at a computing control layer, according to an example embodiment of the present disclosure.
Figure 8B:
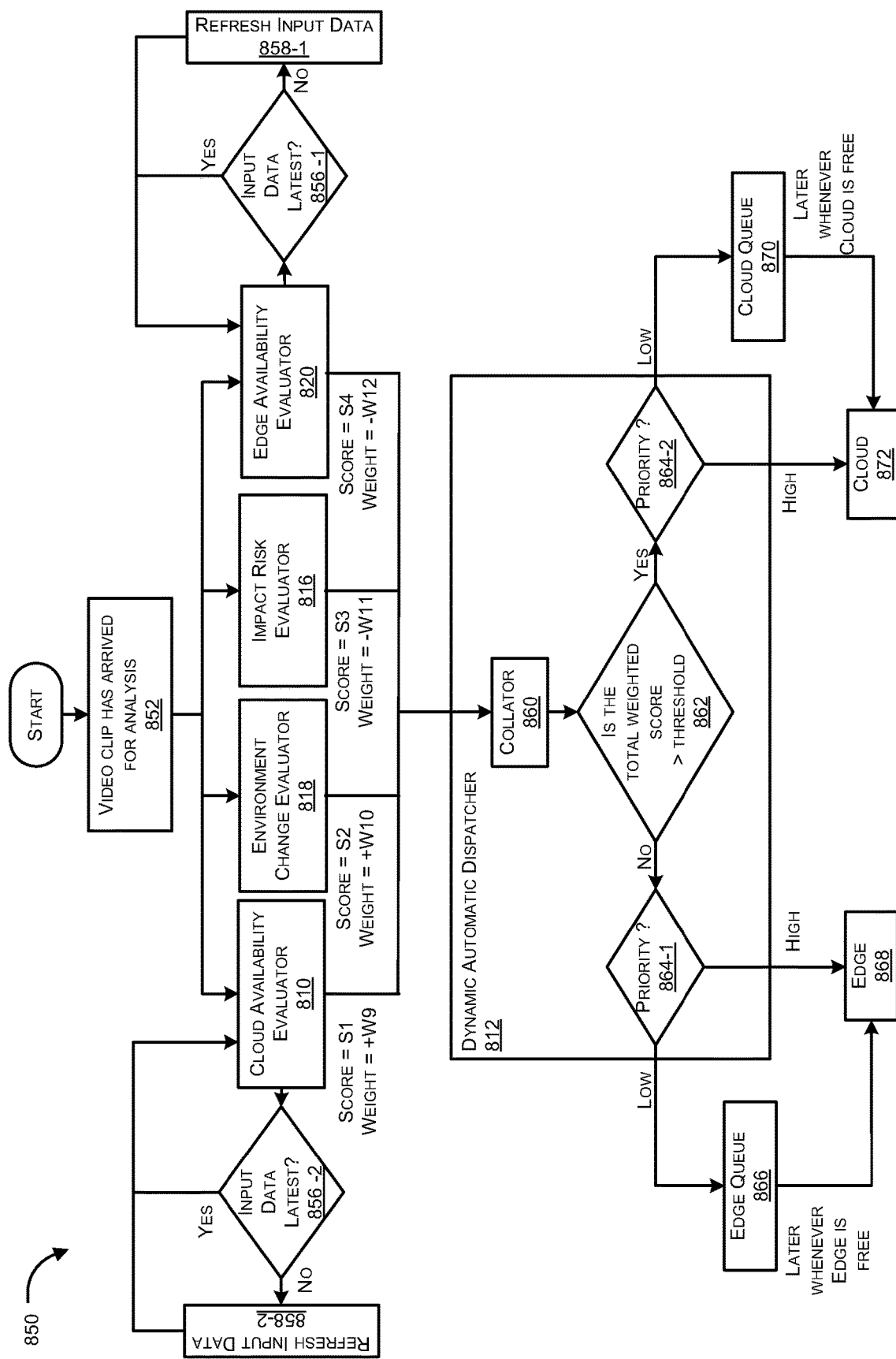
FIG. 8B illustrates a flow diagram showing a functional overview of working of dynamic auto-dispatcher, according to an example embodiment of the present disclosure.

FIG. 8A illustrates a flow diagram 800 showing steps carried out at a computing control layer to obtain computation efficiency, according to an example embodiment of the present disclosure. As illustrated in FIG. 8A, the computing control layer may include a cloud link speed detector 814 which detects if the link speed is less than a predetermined value. If the speed in above the predetermined value, the space risk profiler 300 and the person risk profiler 302 may use the cloud computing mode for assessing interactions (802). If the speed in below the predetermined value, the space risk profiler 300 and the person risk profiler 302 may switch to the edge computing mode for assessing interactions. In an example embodiment and as shown in FIG. 8B, the system 100 may include a dynamic auto-dispatcher 812. The dynamic auto-dispatcher 812 may receive an input information to dynamically determine, in real-time, a working mode suitable for computing the captured information. In an example embodiment, the dynamic auto-dispatcher 812 may automatically switch between the cloud computing mode and the edge computing mode. As shown in FIG. 8A, the input information may be received from at least one sub-module of the system. The at least one sub-module may be a cloud availability evaluator 810, an edge availability evaluator 820, an environment change evaluator 818 and an impact risk evaluator 816. The cloud availability evaluator 810 may evaluate the occupancy of the cloud for the next T minutes (i.e. time required for executing a particular task). The cloud availability evaluator 810 may assess at least one of a historic cloud utilization data 808, cloud macro audit trail data 806 and cloud micro performance metrics 804. The cloud macro audit trail data 806 may be a modern-day cloud platform that may have a tracker such as Cloud Trail. The Cloud Trail may keep track of audit trail of all services and instances that a particular user may be using at an account (macro) level. For example, cloud macro audit trail data 806 can keep track of aspects such as, for example, "How many S3 buckets are active?". "How many instances are running?", "How long it has been in hibernation?", "How much you have it in glaciers?" and other such aspects. The cloud micro performance metrics 804 may be associated with cloud platforms that may have another a tracker such as, for example, "Cloud Watch. The Cloud Watch may monitor micro-level performance metrics in each instance. For example, the micro-level performance metrics may include aspects such as "What is the current CPU utilization?", "What is the current RAM utilization" "How much of storage is currently available?" and other such aspects. The historic cloud utilization data 808 may be a historic data of Cloud CPU and RAM Utilization at various time intervals over a predefined number of days. For example, for a request at 9:55 AM, if upon checking 'Cloud Micro Performance Metrics', it shows that current CPU and RAM utilization as low. However, in the same example, upon checking 'Cloud Utilization Historic Data', it may happen that in next 5 minutes, the cloud utilization will be ~100% for next 45 minutes. This historic data of Cloud CPU and RAM Utilization thus may assist in understanding the trend of utilization of cloud at various time intervals. The edge availability evaluator 820 may evaluate or predict the occupancy or availability of edge computing mode for next T minutes (time required for executing a particular task). The edge availability evaluator 820 may require at least one of current edge utilization data and historic edge utilization data 864 for arriving at a decision. The current edge utilization data may be monitored by an edge observer 826. The edge observer 826 monitors the performance of the edge computing mode and report the utilization metrics. For example, the utilization metrics may include aspects such as "What is the current CPU utilization?", "What is the current RAM utilization" "How much of storage is currently available?" and other such aspects. The historic edge utilization data may be similar in nature to the historic cloud utilization data and may be able to predict occupancy or availability of the edge computing mode in the next T minutes (time required for particular task), based on historical trends of usage. In an example embodiment, the environment change evaluator 818 may use data from the sensors such as, for example, illumination sensor and RF attenuation sensor. The environment change evaluator 818 may evaluate if the environment has changed from a predefined baseline. For example, one or more models associated with the edge computing mode may be capable of only detecting the objects/activities for a given environment. In an instance, there may be a significant deviation in the environment like dim-light or high-light reflecting from person's head or lot of noise (such as, for example, sound of utensils) in the background. However, the computing systems associated with edge computing mode may not be able to identify the object/activities correctly. In that case a video clip (captured information) may need to be pushed to the cloud computing mode for analysis even though the edge computing mode may be available. The environment change evaluator 818 may evaluate these aspects and update the dynamic auto dispatcher 812 accordingly. In an example embodiment, the impact risk evaluator 816 may check various conditions and may evaluate impact risk. If the impact risk may be high, then for faster remediation, local edge-system (edge computing mode) may be preferred over the cloud computing mode. The conditions may consider aspects such as, if a particular space is already marked risky, if the space is over-crowded (people density is high), if the space has persons who are already marked risky and other such conditions. A space-activity map may be utilized to show that the risk impact on the persons at that particular time and space is high. In an embodiment, sensor sampling may be done optimally with help of the data capturer 102. In this case, the cloud databases may be updated only when there may be recognizable change in captured data values, else repeating values may be dropped by gateway. In an embodiment, sensor fusion 822 may be used to handle data reliability such as missing, conflicting, and proxy data as well provide resiliency to sensor failures. In an example embodiment, the dynamic auto-dispatcher 812 may dynamically decide at run-time and automatically dispatch processing load to either the cloud computing mode or edge computing mode. In another example embodiment, the dynamic auto-dispatcher may assign the processing load to a queue for processing for passive processing depending upon the priority.

FIG. 8B illustrates a flow diagram 850 showing a functional overview of working of dynamic auto-dispatcher, according to an example embodiment of the present disclosure. In an example, the space risk profiler 300 and the person risk profiler 302 of the system 100 may interact with a high fidelity video feed analyzer of the cloud computing mode and a low fidelity video analyzer of the edge computing mode. As shown in FIG. 8B, at 852, a video clip (part of the captured information) may be received for analysis. The dynamic auto-dispatcher 812 may include a collator 860. The collator 860 may receive an evaluation input pertaining to the received video clip from the at least one sub-module. The evaluation input received from the cloud availability evaluator 810 may be in the form of score S1 with a weight (+W9). The evaluation input from the cloud availability evaluator 810 may depend on an extent of occupancy of the cloud computing mode for a first imminent time duration. For example, the evaluation input received from the cloud availability evaluator 810 may be obtained by predicting the occupancy or availability of edge computing mode for next T minutes (time required for executing a particular task). In an example embodiment, the evaluation input may be obtained based on at least one of the cloud macro audit trail data 806, the cloud micro performance metrics 804 and the historic cloud utilization data 808 (as explained in FIG. 8A). Prior to obtaining the evaluation input, it may be verified at 856-2, if the input data fed to the edge availability evaluator 820 is latest. If no, the input data may be refreshed at 858-2. The evaluation input received from the edge availability evaluator 820 may be in the form of score S2 with a weight (+W10). The evaluation input from the edge availability evaluator 820 may depend on an extent of occupancy of the edge computing mode for a second imminent time duration. For example, the evaluation input received from the edge availability evaluator 820 may be obtained by predicting the occupancy or availability of edge computing mode for next T minutes (time required for executing a particular task). In an example embodiment, the evaluation input is obtained based on at least one of a current edge utilization data and a historic edge utilization data 824. Prior to obtaining the evaluation input, it may be verified at 856-1, if the input data fed to the edge availability evaluator 820 is latest. If no, the input data may be refreshed at 858-1. The evaluation input received from the environment change evaluator 818 may be in the form of score S3 with a weight (−W11). The evaluation input from the environment change evaluator may include a change in pre-defined attributes of the environment that is derived based on the captured information from the data capturer 102. In an example embodiment, if the change in the pre-defined attributes is observed, the environment change evaluator may recommend the cloud computing mode. In another example embodiment, if the change in the pre-defined attributes is not observed, the environment change evaluator may recommend the edge computing mode. The evaluation input received from the impact risk evaluator 816 may be in the form of score S4 with a weight (−W12). The evaluation input from the impact risk evaluator may depend on the risk factors of the space. In an example embodiment, if the space is associated with a high-risk space profile, the impact risk evaluator may recommend a faster remediation by implementation of the edge computing mode. In another example embodiment, if the space is associated with a low-risk space profile, the impact risk evaluator may recommend the cloud computing mode. Based on the received evaluation input, the collator 860 may determine a final weighted score. For example, the collator may include a machine learning (ML) model that may assign the respective weights and may collate the weighted scores (score S1, S2, S3, S4) and the final weighted score. The final weighted score may be calculated as =(S1×W9+S2×W10−S3×11−S4×W12). The ML model may be trained over a period of time to increase accuracy for estimation of weights and/or threshold. In an example embodiment, the ML model may be trained based on optimizing a cost function and minimizing the total time such as, for example, a sum of waiting time and execution time, for completing the video analytics task. Various other criterion may be considered for training the ML model, based on the requirements. In an example embodiment, based on at least one of the final weighted score (at 862) and a link speed to the cloud computing mode, the dynamic auto-dispatcher 812 may determine the working mode to be the cloud working mode or the edge working mode. If the final weighted score may be greater than a first pre-defined threshold, the dynamic auto-dispatcher may automatically switch to the cloud computing mode (at 864-2). If the final weighted score may be below than the first pre-defined threshold, the dynamic auto-dispatcher may automatically switch to the edge computing mode (at 864-1). At 864-1, a priority of processing may be checked. If the priority is high, the processing may be sent to the edge computing mode directly (868). If the priority is low, the processing may be added to an edge queue (866) and processed later whenever the edge computing mode may be free. At 864-2, a priority of processing may be checked. If the priority is high, the processing may be sent to the cloud computing mode directly (872). If the priority is low, the processing may be added to a cloud queue (870) and processed later whenever the cloud computing mode may be free. In another example embodiment, upon detection of the link speed below a second pre-defined threshold value (not shown), the dynamic auto-dispatcher 812 may automatically switch the working mode to the edge computing mode. In another example embodiment, upon detection the link speed above the second pre-defined threshold value (not shown), the dynamic auto-dispatcher 812 may automatically switch the working mode to the cloud computing mode. In an example, if a total score of 10.0 is considered, if the final weighted score is greater than 5.0, the cloud computing mode may be used and if the final weighted score is equal to or lesser than 5.0 then edge computing mode may be used.

FIG. 9 illustrates a hardware platform 900 for implementation of the system 100, according to an example embodiment of the present disclosure. Particularly, computing machines such as but not limited to internal/external server clusters, quantum computers, desktops, laptops, smartphones, tablets and wearables which may be used to execute the system 100 or may have the structure of the hardware platform 900. The hardware platform 900 may include additional components not shown and that some of the components described may be removed and/or modified. In another example, a computer system with multiple GPUs can sit on external-cloud platforms including Amazon Web Services, or internal corporate cloud computing clusters, or organizational computing resources, etc. In FIG. 9, the hardware platform 900 may be a computer system 900 that may be used with the examples described herein. The computer system 900 may represent a computational platform that includes components that may be in a server or another computer system. The computer system 900 may execute, by a processor (e.g., a single or multiple processors) or other hardware processing circuit, the methods, functions and other processes described herein. These methods, functions and other processes may be embodied as machine-readable instructions stored on a computer-readable medium, which may be non-transitory, such as hardware storage devices (e.g., RAM (random access memory), ROM (read-only memory), EPROM (erasable, programmable ROM), EEPROM (electrically erasable, programmable ROM), hard drives, and flash memory). The computer system 900 may include a processor 905 that executes software instructions or code stored on a non-transitory computer-readable storage medium 910 to perform methods of the present disclosure. The software code includes, for example, instructions to gather information pertaining risk factors and data elements in an environment and generate alerts, based on risk assessment of the environment. In an example, one or more of the data capturer 102, the data warehouse 104, the process engine 106, and the output device 108 may be software codes or components performing these steps.

The instructions on the computer-readable storage medium 910 are read and stored the instructions in storage 915 or in random access memory (RAM) 920. The storage 915 provides a large space for keeping static data where at least some instructions could be stored for later execution. The stored instructions may be further compiled to generate other representations of the instructions and dynamically stored in the RAM 920. The processor 905 reads instructions from the RAM 920 and performs actions as instructed.

The computer system 900 further includes an output device 925 to provide at least some of the results of the execution as output including, but not limited to, visual information to users, such as external agents. The output device can include a display on computing devices and virtual reality glasses. For example, the display can be a mobile phone screen or a laptop screen. GUIs and/or text are presented as an output on the display screen. The computer system 900 further includes input device 930 to provide a user or another device with mechanisms for entering data and/or otherwise interact with the computer system 900. The input device may include, for example, a keyboard, a keypad, a mouse, or a touchscreen. In an example, output of any of the data capturer 102, the process engine 106, and the output device 108 may be displayed on the output device 925. Each of these output devices 925 and input devices 930 could be joined by one or more additional peripherals. In an example, the output device 925 may be used to provide alerts or display a risk assessment map of the environment.

A network communicator 935 may be provided to connect the computer system 900 to a network and in turn to other devices connected to the network including other clients, servers, data stores, and interfaces, for instance. A network communicator 935 may include, for example, a network adapter such as a LAN adapter or a wireless adapter. The computer system 900 includes a data source interface 940 to access data source 945. A data source is an information resource. As an example, a database of exceptions and rules may be a data source. Moreover, knowledge repositories and curated data may be other examples of data sources.

Figure 10:
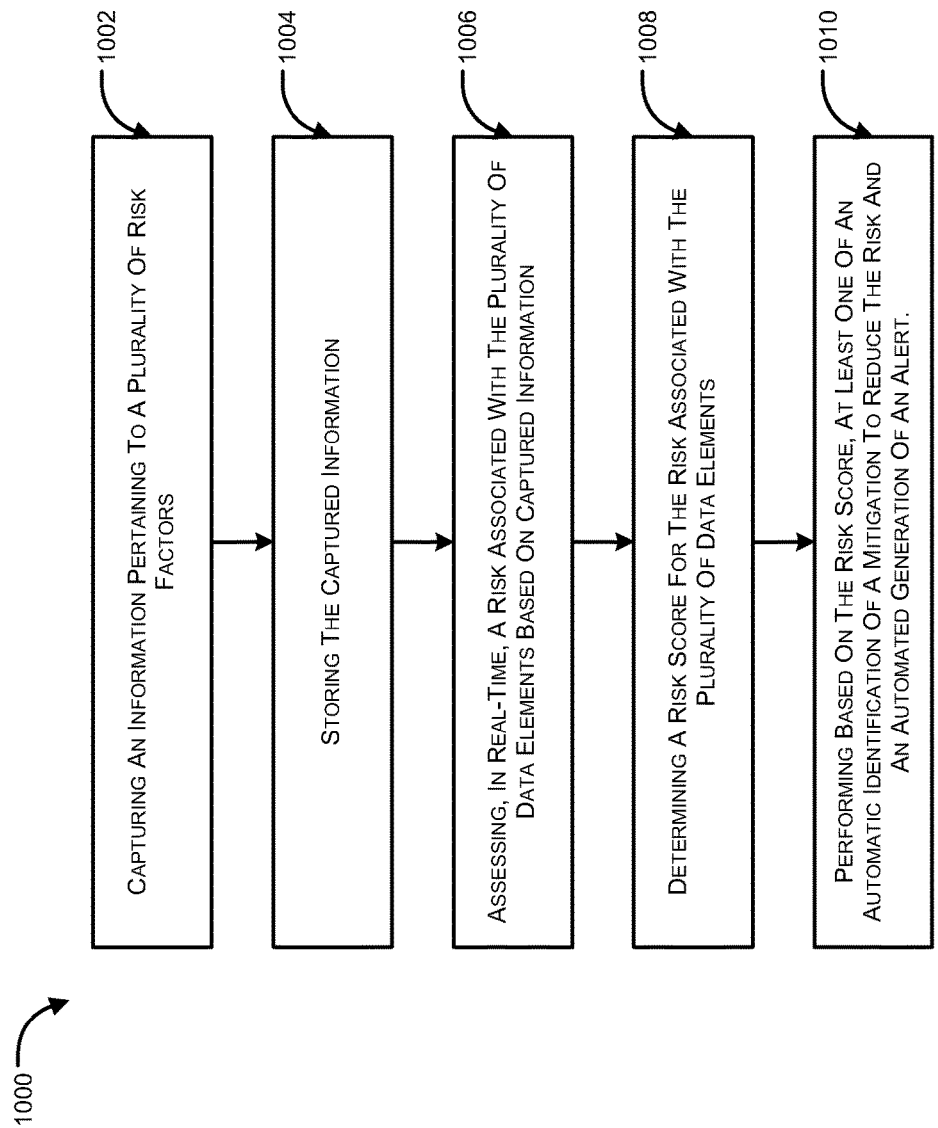
FIG. 10 illustrates a flow diagram for facilitating a dynamic risk assessment, according to an example embodiment of the present disclosure.

FIG. 10 illustrates a flow diagram (1000) for facilitating a dynamic risk assessment, according to an example embodiment of the present disclosure. At 1002, the method includes a step of capturing, by a processor, information pertaining to a plurality of risk factors associated with an infection risk corresponding to a plurality of data elements in an environment. The plurality of data elements may pertain to at least one of a space and a person in the space. At 1004, the method includes a step of determining, by the processor, a risk score associated with the infection risk corresponding to the plurality of data elements. The risk score may include a space risk score corresponding to the space and a person risk score associated with the person. The risk score may be a weighted function of the corresponding risk factors. At 1006, the method includes a step of determining, by the processor, based on the space risk score, a space risk profile associated with the space. At 1008, the method includes a step of determining, by the processor, based on the person risk score, a person risk profile associated with the person. At 1010, the method includes a step of performing, by the processor, based on the risk profile, at least one of an automatic identification of a mitigation to reduce the infection risk and an automated generation of an alert. In an example, embodiment, in addition to generating an alert automatically or alternatively, the present disclosure may also automatically take actions to reduce the risk of an infection. This may include, for example, automatically sealing a facility that poses a high risk of infections by activating locks on the doors to the facility; automatically restricting access of persons with a high risk score to certain facilities by deactivating access of such persons. This may be done for example, by deactivating access cards, passwords, and other access techniques used by persons to enter secure premises. One of ordinary skill in the art will appreciate that other automated actions may be taken by the present disclosure to reduce the risk of infection without departing from the scope of the disclosure.

The order in which the steps of the method 1000 are described is not intended to be construed as a limitation, and any number of the described method blocks may be combined or otherwise performed in any order to implement the method 1000, or an alternate method. Additionally, individual blocks may be deleted from the methods 1000 without departing from the spirit and scope of the present disclosure described herein. Furthermore, the method 1000 may be implemented in any suitable hardware, software, firmware, or a combination thereof, that exists in the related art or that is later developed. The method 1000 describe, without limitation, the implementation of the system 100. A person of skill in the art will understand that method 1000 may be modified appropriately for implementation in various manners without departing from the scope and spirit of the disclosure.

What has been described and illustrated herein are examples of the present disclosure. One of ordinary skill in the art will appreciate that techniques consistent with the present disclosure are applicable in other contexts as well without departing from the scope of the disclosure. The terms, descriptions, and figures used herein are set forth by way of illustration only and are not meant as limitations. Many variations are possible within the spirit and scope of the subject matter, which is intended to be defined by the following claims and their equivalents in which all terms are meant in their broadest reasonable sense unless otherwise indicated.

We claim:

1. A system comprising:
   a processor;
   a memory coupled to the processor, wherein the memory comprises a computer-readable instructions in form of a plurality of modules comprising:
   a data capturer module coupled to a processor, the data capturer module to capture information pertaining to a plurality of risk factors associated with an infection risk corresponding to a plurality of data elements in an environment, wherein the plurality of data elements pertain to a space and a person in the space;
   a data warehouse module coupled to the processor and to store the captured information; and
   a process engine of the processor, the process engine comprising a space risk profiler and a person risk profiler, the process engine to:
      determine a risk score associated with the infection risk corresponding to the plurality of data elements, wherein the risk score includes a space risk score corresponding to the space and a person risk score associated with the person, the risk score being a weighted function of corresponding risk factors wherein the risk score is determined using a machine-learning model and wherein the plurality of data elements correspond to a fine granular type of data elements and wherein the risk score is determined based on the space and the person in the space;
      determine, using the space risk profiler, based on the space risk score, a space risk profile associated with the space; and
      determine, using the person risk profiler, based on the person risk score, a person risk profile associated with the person,
   wherein the process engine is coupled to the data warehouse module to automatically update the space risk profile and the person risk profile, and
   wherein based on the space risk profile and the person risk profile, the processor performs at least one of an automatic identification of a mitigation to reduce the infection risk and an automated generation of an alert, wherein the process engine comprises:
   a matrix generator coupled to the processor to:
   receive a label associated with the space risk profile and the person risk profile; and assess the infection risk by generating a person risk vector, a space risk vector, a person-person risk matrix, and a person-space risk matrix based on the label;

an advisory generator coupled to the processor to generate a personalized advisory upon receipt of a personalized advisory trigger from an output device; and a downstream activator coupled to the processor to provide actions to minimize the infection risk upon receipt of identified mitigation.

2. The system as claimed in claim 1, wherein the data capturer comprises at least one of a sensor and a tracking device, wherein the data capturer is at least one of a Radio-frequency identification (RFID) sensor, Bluetooth Low Energy (BLE) sensor, machine learning (MIL) based computer vision sensor, a visual sensor, a camera, and a closed-circuit television (CCTV).

3. The system as claimed in claim 1, wherein the plurality of data elements associated with the space includes a space transit time data and a building plan data, and the plurality of data elements associated with the person includes an attire data, an indoor movement data, an interaction data, hygiene and behavior data, and a network centrality data indicating an extent of social interactions of the at least one person.

4. The system as claimed in claim 3, wherein the space transit time data pertains to a logged time duration spent by the person in the space, the attire data pertains to verification of a recommended attire for the person, the building plan data pertains to a constructional layout of the space and a list of amenities available in the space, the indoor movement data pertains to tracked information associated with a path trajectory taken by the person within the space, the interaction data pertains to a record of an interaction between two or more persons, the hygiene and behavior data pertains to a behavioral aspect related to maintenance of hygiene by the person, and the network centrality data relates to assessment of a social interactive ability of the person.

5. The system of claim 4, wherein the data warehouse module comprises:
a Building Management System (BMS) repository configured to store the building plan data;
a social interactions repository to store the interaction data and the network centrality data;
a space transit timing repository to store the space transit time data;
an hourly based density repository to store the indoor movement data;
a sterilization repository to store the hygiene and behavior data;
a people risk profile repository to store the person risk profile; and
a space risk profile repository to store the space risk profile, wherein the space risk profiler and the person risk profiler automatically update the space risk profile and the person risk profile in the space risk profile repository and the people risk profile repository respectively.

6. The system of claim 5, wherein the space risk profiler comprises a space color assigner to assign a color based indication based on the space risk profile,
wherein the color based indication indicates an extent of a safety or the infection risk pertaining to the space, and
wherein the color based indication is generated by the space color assigner, as per a first schedule, and by an interaction including at least one of:

an interaction with the space transit timings repository to assign a first score based on an average risk profile of the person present in the space at a pre-defined time duration;
an interaction with the people risk profile repository to assign a second score based on identification of an infected person from the person in the space, wherein the second score corresponds to a time duration spent by the infected person in the space;
an interaction with the hourly based density repository to assign a third score based on average hourly density of the persons present in the space for a time period;
an interaction with the BMS repository to assign a fourth score based on predefined attributes including at least one of a ventilation type of the space and time duration for which air conditioning is switched ON in the space; and
an interaction with the sterilization repository to assign a fifth score based on an extent of time duration passed after sanitization of the space.

7. The system of claim 6, wherein the process engine computes an average of the first score, the second score, the third score, the fourth score and the fifth score to generate a first average weighted score based on respective weight assigned to each interaction, the respective weight being assigned by a first model of the space risk profiler, wherein the first model is a linear regression model trained based on machine learning,
wherein, a rules engine of the processor, based on the first average weighted score and a first set of pre-defined rules, assigns a predefined color pertaining to the color based indication, and
wherein a subsequent schedule to the first schedule for assigning the color pertaining to the color based indication is dependent on historical color data, total number of high-risk persons and infected persons in the space and a nature of the space.

8. The system of claim 7, wherein the color based indication is updated in the space risk profile repository of the data warehouse module at predefined time intervals.

9. The system of claim 5, wherein the person risk profiler comprises a person risk assigner to assign the person risk profile to the person as per a second schedule and by an interaction including at least one of:
an interaction with the people risk profile repository to assign a sixth score based on average risk profile of the person interacting with another person in a pre-defined time duration;
an interaction with the space transit timings repository to assign a seventh score based on an average risk profile of the space where the person physically enters or exits the space in a pre-defined time duration; and
an interaction with the social interactions repository to assign an eighth score based on time duration spent by the person with the infected person;
wherein the processor computes an average of the sixth score, the seventh score and the eighth score to generate a second average weighted score based on respective weight assigned to each interaction, the respective weight being assigned by a second model of the person risk profiler, wherein the second model is a linear regression model trained based on machine learning,
wherein, the rules engine of the processor, based on the second average weighted score and a second set of pre-defined rules, assigns the person risk profile to the person.

10. The system of claim 9, wherein the processor determines a subsequent schedule to the second schedule based on at least one of a historical risk data, total number of high-risk profile of persons in the space and a nature of the person.

11. The system of claim 1, wherein the space risk profiler is coupled to the data warehouse module and comprises:
- a first space transit time recorder to be triggered when the person performs an action including at least one of entering the space and exiting the space, wherein the action is sensed by the data capturer;
- a density evaluator to:
  - interact with the space transit timings repository to periodically evaluate a density of the persons in the space; and
  - store, in the hourly people-density repository of the data warehouse module, a space identity associated with the space and an average number of the persons entering or exiting the space per hour;
- a first unsafe events recorder to be triggered upon detection of a first pre-defined unsafe event in the space, wherein the first pre-defined unsafe event pertains to non-compliance of a safety measure; and
- a sterilization recorder to be triggered upon detection of a sterilization event pertaining to the space.

12. The system of claim 11, wherein a person risk profiler is coupled to the data warehouse module and comprises:
- a second space transit time recorder that is triggered when the person performs an action including at least one of entering the space and exiting the space, wherein the action is sensed by the data capturer;
- an interactions recorder that is triggered when a distance between two persons crosses a predefined threshold distance, wherein at least one of the two persons is identified to include corresponding high risk profile;
- a second unsafe events recorder that is triggered, upon detection of a second pre-defined unsafe event pertaining to the person, wherein the second pre-defined unsafe event pertains to non-compliance of at least one safety measure by the person; and
- an infection updater that is updated upon detecting a presence of the infected person.

13. The system of claim 12, wherein the second unsafe events recorder, upon detection of the second pre-defined unsafe event, sends a first interrupt signal to notify the person risk assigner of at least one of a medium risk profile and a high risk profile of the person associated with the second pre-defined unsafe event, based on severity of the second pre-defined unsafe event.

14. The system of claim 12, wherein the infection updater, upon detection of the infected person, sends a second interrupt signal to the person risk assigner to update the person risk profile and to raise a flag indicating a high infection risk.

15. The system of claim 1, wherein the system comprises a dynamic auto-dispatcher that receives an input information to dynamically determine, in real-time, a working mode suitable for computing the captured information, wherein the working mode comprises at least one of a cloud computing mode and an edge computing mode, wherein the dynamic auto-dispatcher automatically switches between the cloud computing mode and the edge computing mode,
- wherein the input information is received from at least one sub-module of the system, wherein the at least one sub-module is a cloud availability evaluator, an edge availability evaluator, an environment change evaluator and an impact risk evaluator,
- wherein a collator of the dynamic auto-dispatcher receives an evaluation input from the at least one sub-module and determines a final weighted score based on the received evaluation input,
- wherein based on at least one of the final weighted score and a link speed to the cloud computing mode, the dynamic auto-dispatcher determines the working mode to be the cloud working mode or the edge working mode,
- wherein if the total weighted score is greater than a first pre-defined threshold, the dynamic auto-dispatcher automatically switches to the cloud computing mode, wherein if the final weighted score is below than the first pre-defined threshold, the dynamic auto-dispatcher automatically switches to the edge computing mode,
- wherein the dynamic auto-dispatcher, upon detection of the link speed below a second pre-defined threshold value, automatically switches the working mode to the edge computing mode, and
- wherein the dynamic auto-dispatcher, upon detection the link speed above the second pre-defined threshold value, the dynamic auto-dispatcher automatically switches the working mode to the cloud computing mode.

16. The system of claim 15,
- wherein the evaluation input from the cloud availability evaluator depends on an extent of occupancy of the cloud computing mode for a first imminent time duration, wherein the evaluation input is obtained based on at least one of a cloud macro audit trail data, a cloud micro performance metrics and a historic cloud utilization data;
- wherein the evaluation input from the edge availability evaluator depends on an extent of occupancy of the edge computing mode for a second imminent time duration, wherein the evaluation input is obtained based on at least one of a current edge utilization data and a historic edge utilization data;
- wherein the evaluation input from the environment change evaluator depends on the captured information from the data capturer, a change in pre-defined attributes of the environment, wherein if the change in the pre-defined attributes is observed, the environment change evaluator recommends the cloud computing mode, wherein if the change in the pre-defined attributes is not observed, the environment change evaluator recommends the edge computing mode; and
- wherein the evaluation input from the impact risk evaluator depends on the risk factors of the space, wherein if the space is associated with a high-risk space profile, the impact risk evaluator recommends a faster remediation by implementation of the edge computing mode, wherein if the space is associated with a low-risk space profile, the impact risk evaluator recommends the cloud computing mode.

17. A method for facilitating a dynamic risk assessment, the method comprising:
- capturing, by a processor, information pertaining to a plurality of risk factors associated with an infection risk corresponding to a plurality of data elements in an environment, wherein the plurality of data elements pertains to a space and a person in the space,
- determining, by the processor, a risk score associated with the infection risk corresponding to the plurality of data elements, wherein the risk score includes a space risk score corresponding to the space and a person risk score associated with the person, the risk score being a weighted function of corresponding risk factors, wherein the risk score is determined using a machine-learning model and wherein the plurality of data elements correspond to a fine granular type of data elements and wherein the risk score is determined based on the space and the person in the space;

determining, by the processor, based on the space risk score, a space risk profile associated with the space;

determining, by the processor, based on the person risk score, a person risk profile associated with the person;

performing, by the processor, based on the space risk profile and the person risk profile, at least one of an automatic identification of a mitigation to reduce the infection risk and an automated generation of an alert, receiving, by the processor, a label associated with the space risk profile and the person risk profile;

assessing, by the processor, the infection risk by generating a person risk vector, a space risk vector, a person-person risk matrix, and a person-space risk matrix based on the label;

generating, by the processor, a personalized advisory upon receipt of a personalized advisory trigger from an output device; and providing, by the processor, actions to minimize the infection risk upon receipt of identified mitigation.

18. A non-transitory computer readable medium, wherein the readable medium comprises machine executable instructions that are executable by a processor to:

capture information pertaining to a plurality of risk factors associated with an infection risk corresponding to a plurality of data elements in an environment, wherein the plurality of data elements pertains to a space and a person in the space, determine a risk score associated with the infection risk corresponding to the plurality of data elements, wherein the risk score includes a space risk score corresponding to the space and a person risk score associated with the person, the risk score being a weighted function of corresponding risk factors, wherein the risk score is determined using a machine-learning model and wherein the plurality of data elements correspond to a fine granular type of data elements and wherein the risk score is determined based on the space and the person in the space;

determine, based on the space risk score, a space risk profile associated with the space;

determine, based on the person risk score, a person risk profile associated with the person;

perform, based on the space risk profile and the person risk profile, at least one of an automatic identification of a mitigation to reduce the infection risk and an automated generation of an alert; receiving, by the processor, a label associated with the space risk profile and the person risk profile;

assess the infection risk by generating a person risk vector, a space risk vector, a person-person risk matrix, and a person-space risk matrix based on the label;

generate a personalized advisory upon receipt of a personalized advisory trigger from an output device; and provide actions to minimize the infection risk upon receipt of the identified mitigation.

* * * * *